US011783938B2

(12) United States Patent
Shelton, IV et al.

(10) Patent No.: US 11,783,938 B2
(45) Date of Patent: Oct. 10, 2023

(54) INTEGRATED HUB SYSTEMS CONTROL INTERFACES AND CONNECTIONS

(71) Applicant: Cilag GmbH International, Zug (CH)

(72) Inventors: Frederick E. Shelton, IV, Hillsboro, OH (US); Kevin Fiebig, Cincinnati, OH (US)

(73) Assignee: Cilag GmbH International, Zug (CH)

( * ) Notice: Subject to any disclaimer, the term of this patent is extended or adjusted under 35 U.S.C. 154(b) by 118 days.

(21) Appl. No.: 17/384,164

(22) Filed: Jul. 23, 2021

(65) Prior Publication Data

US 2023/0028677 A1  Jan. 26, 2023

Related U.S. Application Data

(60) Provisional application No. 63/224,813, filed on Jul. 22, 2021.

(51) Int. Cl.
*G06F 3/14* (2006.01)
*G16H 40/20* (2018.01)
(Continued)

(52) U.S. Cl.
CPC ............ *G16H 40/20* (2018.01); *A61B 17/00* (2013.01); *A61B 18/1206* (2013.01);
(Continued)

(58) Field of Classification Search
None
See application file for complete search history.

(56) References Cited

U.S. PATENT DOCUMENTS

| 6,766,373 B1 | 7/2004 | Beadle et al. |
| 8,565,073 B2 | 10/2013 | Rahman et al. |

(Continued)

FOREIGN PATENT DOCUMENTS

| JP | 2017504019 A5 | 12/2017 |
| WO | 2013174327 A1 | 11/2013 |

(Continued)

OTHER PUBLICATIONS

U.S. Appl. No. 17/384,354, filed Jul. 23, 2021, Shelton IV et al.
(Continued)

*Primary Examiner* — Scott C Sun
(74) *Attorney, Agent, or Firm* — Condo Roccia Koptiw LLP

(57) ABSTRACT

Systems, methods, and instrumentalities are disclosed for switching a control scheme to control a set of system modules and/or modular devices of a surgical hub. A surgical hub may determine a first control scheme that is configured to control a set of system modules and/or modular devices. The surgical hub may receive an input from one of the set of modules or a device located in an OR. The surgical hub may make a determination that at least one of a safety status level or an overload status level of the surgical hub is higher than its threshold value. Based on at least the received input and the determination, the surgical hub may determine a second control scheme to be used to control the set of system modules. The surgical hub may send a control program indicating the second control scheme to one or more system modules and/or modular devices.

20 Claims, 14 Drawing Sheets

(51) Int. Cl.

| | | |
|---|---|---|
| *G16H 20/40* | (2018.01) | |
| *A61B 34/10* | (2016.01) | |
| *A61B 34/32* | (2016.01) | |
| *G16H 50/70* | (2018.01) | |
| *G16H 50/20* | (2018.01) | |
| *A61B 34/30* | (2016.01) | |
| *G16H 30/40* | (2018.01) | |
| *G06N 20/00* | (2019.01) | |
| *A61B 17/00* | (2006.01) | |
| *H04L 1/22* | (2006.01) | |
| *H04L 65/80* | (2022.01) | |
| *H04N 7/15* | (2006.01) | |
| *A61B 90/00* | (2016.01) | |
| *G16H 40/40* | (2018.01) | |
| *G06F 13/40* | (2006.01) | |
| *G16H 40/67* | (2018.01) | |
| *G16H 10/60* | (2018.01) | |
| *G16H 15/00* | (2018.01) | |
| *G06F 16/28* | (2019.01) | |
| *G05B 13/02* | (2006.01) | |
| *H04L 41/12* | (2022.01) | |
| *H04L 67/12* | (2022.01) | |
| *A61B 34/20* | (2016.01) | |
| *A61B 34/00* | (2016.01) | |
| *G06Q 10/30* | (2023.01) | |
| *G06T 11/60* | (2006.01) | |
| *G06F 16/21* | (2019.01) | |
| *G16H 40/63* | (2018.01) | |
| *H04N 5/272* | (2006.01) | |
| *A61B 18/12* | (2006.01) | |
| *G06F 3/16* | (2006.01) | |
| *G08B 5/22* | (2006.01) | |
| *G10L 15/22* | (2006.01) | |
| *G06F 9/48* | (2006.01) | |
| *G06F 9/54* | (2006.01) | |
| *H04L 67/125* | (2022.01) | |
| *A61B 8/06* | (2006.01) | |
| *G16H 30/20* | (2018.01) | |
| *G06F 40/169* | (2020.01) | |
| *G06F 21/62* | (2013.01) | |
| *A61B 18/00* | (2006.01) | |
| *H02J 7/00* | (2006.01) | |

(52) U.S. Cl.
CPC .............. *A61B 34/10* (2016.02); *A61B 34/20* (2016.02); *A61B 34/25* (2016.02); *A61B 34/30* (2016.02); *A61B 34/32* (2016.02); *A61B 90/08* (2016.02); *A61B 90/37* (2016.02); *G05B 13/0265* (2013.01); *G06F 3/14* (2013.01); *G06F 3/1423* (2013.01); *G06F 3/167* (2013.01); *G06F 9/4881* (2013.01); *G06F 9/542* (2013.01); *G06F 13/4068* (2013.01); *G06F 16/211* (2019.01); *G06F 16/284* (2019.01); *G06F 16/285* (2019.01); *G06N 20/00* (2019.01); *G06Q 10/30* (2013.01); *G06T 11/60* (2013.01); *G08B 5/22* (2013.01); *G10L 15/22* (2013.01); *G16H 10/60* (2018.01); *G16H 15/00* (2018.01); *G16H 20/40* (2018.01); *G16H 30/40* (2018.01); *G16H 40/40* (2018.01); *G16H 40/63* (2018.01); *G16H 40/67* (2018.01); *G16H 50/20* (2018.01); *G16H 50/70* (2018.01); *H04L 1/22* (2013.01); *H04L 41/12* (2013.01); *H04L 65/80* (2013.01); *H04L 67/12* (2013.01); *H04L 67/125* (2013.01); *H04N 5/272* (2013.01); *H04N 7/15* (2013.01); *A61B 8/06* (2013.01); *A61B 2017/00221* (2013.01); *A61B 2018/00702* (2013.01); *A61B 2018/00994* (2013.01); *A61B 2034/2072* (2016.02); *A61B 2034/254* (2016.02); *A61B 2090/364* (2016.02); *A61B 2090/365* (2016.02); *A61B 2090/373* (2016.02); *G06F 21/6245* (2013.01); *G06F 40/169* (2020.01); *G10L 2015/223* (2013.01); *G16H 30/20* (2018.01); *H02J 7/0063* (2013.01)

(56) References Cited

U.S. PATENT DOCUMENTS

| | | | |
|---|---|---|---|
| 8,908,678 | B1 | 12/2014 | Mcgonigal et al. |
| 9,011,427 | B2 | 4/2015 | Price et al. |
| 9,283,054 | B2 | 3/2016 | Morgan et al. |
| 9,345,481 | B2 | 5/2016 | Hall et al. |
| 11,146,690 | B2 | 10/2021 | Minert |
| 2002/0000464 | A1 | 1/2002 | Ramberg et al. |
| 2005/0210070 | A1 | 9/2005 | Macneil |
| 2013/0051220 | A1 | 2/2013 | Ryshakov |
| 2013/0149967 | A1 | 6/2013 | Ma et al. |
| 2014/0160259 | A1 | 6/2014 | Blanquart et al. |
| 2014/0160260 | A1 | 6/2014 | Blanquart et al. |
| 2014/0263552 | A1 | 9/2014 | Hall et al. |
| 2014/0267655 | A1 | 9/2014 | Richardson et al. |
| 2015/0128274 | A1 | 5/2015 | Giokas |
| 2015/0182118 | A1 | 7/2015 | Bradbury et al. |
| 2015/0215159 | A1 | 7/2015 | Liao et al. |
| 2017/0296213 | A1 | 10/2017 | Swensgard et al. |
| 2018/0344308 | A1 | 12/2018 | Nawana et al. |
| 2018/0360452 | A1 | 12/2018 | Shelton, IV et al. |
| 2019/0019163 | A1 | 6/2019 | Kuhn et al. |
| 2019/0191963 | A1 | 6/2019 | Kuhn et al. |
| 2019/0200844 | A1 | 7/2019 | Shelton, IV et al. |
| 2019/0200906 | A1 | 7/2019 | Shelton, IV et al. |
| 2019/0200980 | A1 | 7/2019 | Shelton, IV et al. |
| 2019/0200988 | A1 | 7/2019 | Shelton, IV |
| 2019/0201033 | A1 | 7/2019 | Yates et al. |
| 2019/0201102 | A1 | 7/2019 | Shelton, IV et al. |
| 2019/0201104 | A1 | 7/2019 | Shelton, IV et al. |
| 2019/0201115 | A1 | 7/2019 | Shelton, IV et al. |
| 2019/0201123 | A1 | 7/2019 | Shelton, IV et al. |
| 2019/0201124 | A1 | 7/2019 | Shelton, IV et al. |
| 2019/0201125 | A1 | 7/2019 | Shelton, IV et al. |
| 2019/0201126 | A1 | 7/2019 | Shelton, IV et al. |
| 2019/0201127 | A1 | 7/2019 | Shelton, IV et al. |
| 2019/0201129 | A1 | 7/2019 | Shelton, IV et al. |
| 2019/0201137 | A1 | 7/2019 | Shelton, IV et al. |
| 2019/0201140 | A1 | 7/2019 | Yates et al. |
| 2019/0204201 | A1 | 7/2019 | Shelton, IV et al. |
| 2019/0205441 | A1 | 7/2019 | Shelton, IV et al. |
| 2019/0205566 | A1 | 7/2019 | Shelton, IV et al. |
| 2019/0205567 | A1 | 7/2019 | Shelton, IV et al. |
| 2019/0206216 | A1 | 7/2019 | Shelton, IV et al. |
| 2019/0206542 | A1 | 7/2019 | Shelton, IV et al. |
| 2019/0206551 | A1 | 7/2019 | Yates et al. |
| 2019/0206556 | A1 | 7/2019 | Shelton, IV et al. |
| 2019/0206562 | A1 | 7/2019 | Shelton, IV et al. |
| 2019/0206569 | A1 | 7/2019 | Shelton, IV et al. |
| 2019/0206576 | A1 | 7/2019 | Shelton, IV et al. |
| 2019/0207773 | A1 | 7/2019 | Shelton, IV et al. |
| 2019/0207911 | A1 | 7/2019 | Wiener et al. |
| 2020/0244734 | A1 | 7/2020 | Mendiola et al. |
| 2020/0405403 | A1* | 12/2020 | Shelton, IV ........... A61B 46/10 |
| 2021/0290046 | A1 | 9/2021 | Nazareth et al. |
| 2022/0046292 | A1 | 2/2022 | Nair et al. |
| 2022/0104713 | A1 | 4/2022 | Shelton, IV |
| 2022/0104807 | A1 | 4/2022 | Shelton, IV et al. |
| 2022/0104896 | A1 | 4/2022 | Shelton, IV et al. |
| 2022/0104910 | A1 | 4/2022 | Shelton, IV et al. |
| 2022/0233119 | A1 | 7/2022 | Shelton, IV et al. |
| 2022/0233135 | A1 | 7/2022 | Shelton, IV et al. |
| 2022/0233136 | A1 | 7/2022 | Shelton, IV et al. |
| 2022/0233151 | A1 | 7/2022 | Shelton, IV et al. |

(56) References Cited

U.S. PATENT DOCUMENTS

| | | |
|---|---|---|
| 2022/0233191 A1 | 7/2022 | Shelton, IV et al. |
| 2022/0233252 A1 | 7/2022 | Shelton, IV et al. |
| 2022/0233254 A1 | 7/2022 | Shelton, IV et al. |
| 2022/0238216 A1 | 7/2022 | Shelton, IV et al. |
| 2022/0240869 A1 | 8/2022 | Shelton, IV et al. |
| 2022/0241028 A1 | 8/2022 | Shelton, IV et al. |
| 2022/0241474 A1 | 8/2022 | Shelton, IV et al. |
| 2022/0303945 A1 | 9/2022 | Tsuda |
| 2023/0021832 A1 | 1/2023 | Shelton, IV et al. |
| 2023/0021920 A1 | 1/2023 | Shelton, IV et al. |
| 2023/0022604 A1 | 1/2023 | Shelton, IV |
| 2023/0023083 A1 | 1/2023 | Shelton, IV et al. |
| 2023/0023635 A1 | 1/2023 | Shelton, IV et al. |
| 2023/0025061 A1 | 1/2023 | Shelton, IV et al. |
| 2023/0025790 A1 | 1/2023 | Shelton, IV et al. |
| 2023/0025827 A1 | 1/2023 | Shelton, IV et al. |
| 2023/0026634 A1 | 1/2023 | Shelton, IV et al. |
| 2023/0026893 A1 | 1/2023 | Shelton, IV et al. |
| 2023/0027210 A1 | 1/2023 | Shelton, IV et al. |
| 2023/0027543 A1 | 1/2023 | Shelton, IV et al. |
| 2023/0028059 A1 | 1/2023 | Shelton, IV et al. |
| 2023/0028633 A1 | 1/2023 | Shelton, IV et al. |

FOREIGN PATENT DOCUMENTS

| | | |
|---|---|---|
| WO | 2017089479 A1 | 6/2017 |
| WO | 2019/119130 A1 | 6/2019 |
| WO | 2021048326 A1 | 3/2021 |

OTHER PUBLICATIONS

U.S. Appl. No. 17/384,453, filed Jul. 23, 2021, Shelton IV et al.
U.S. Appl. No. 17/384,455, filed Jul. 23, 2021, Shelton IV et al.
U.S. Appl. No. 17/384,457, filed Jul. 23, 2021, Shelton IV et al.
U.S. Appl. No. 17/384,508, filed Jul. 23, 2021, Shelton IV et al.
U.S. Appl. No. 17/384,553, filed Jul. 23, 2021, Shelton IV et al.
U.S. Appl. No. 17/384,128, filed Oct. 15, 2020, Shelton IV et al.
U.S. Appl. No. 17/384,142, filed Jul. 23, 2021, Shelton IV et al.
U.S. Appl. No. 17/384,151, filed Jul. 23, 2021, Shelton IV et al.
U.S. Appl. No. 17/384,270, filed Jul. 23, 2021, Shelton IV et al.
U.S. Appl. No. 17/384,274, filed Jul. 23, 2021, Shelton IV et al.
U.S. Appl. No. 17/384,337, filed Jul. 23, 2021, Shelton IV et al.
U.S. Appl. No. 17/384,265, filed Jul. 23, 2021, Shelton IV et al.
U.S. Appl. No. 17/384,348, filed Jul. 23, 2021, Shelton IV et al.
U.S. Appl. No. 62/611,341, filed Dec. 28, 2017, Shelton IV et al.
Jagannath et al., "An Analysis of Speech as a Modality for Activity Recognition during Complex Medical Teamwork", Pervasive Computing Technologies for Healthcare, May 2018, pp. 1-10.

* cited by examiner

INTEGRATED HUB SYSTEMS CONTROL INTERFACES AND CONNECTIONS

CROSS-REFERENCE TO RELATED APPLICATIONS

This application claims the benefit of Provisional U.S. Patent Application No. 63/224,813, filed Jul. 22, 2021, the disclosure of which is incorporated herein by reference in its entirety.

BACKGROUND

Medical facilities may contain multiple operating rooms (ORs). The ORs may be designated for specific medical specialties, for example, a thoracic surgery. ORs may use procedure-specific surgical systems that are based on the type of surgical procedure to be performed. For example, a surgical system for a thoracic surgical procedure in a thoracis OR may be different from a surgical system used for a colorectal surgical procedure in a colorectal OR. The surgical systems in each OR may have a plurality of system modules and/or modular devices. There may be a need for establishing mechanisms for the selection of the system modules and/or modular devices to be utilized for a particular surgical procedure and how the system modules and/or modular devices may be controlled.

SUMMARY

Systems, methods, and instrumentalities are disclosed for switching (e.g., adaptively switching) a control scheme to control a set of system modules and/or modular devices associated with a surgical hub. In an example, a surgical hub may determine a first control scheme that is configured to control a set of system modules and/or modular devices associated with the surgical hub.

The surgical hub may receive an input from one of the set of modules or a device that is located within bounds of an operating room. The surgical hub may determine that a safety status level and/or an overload status level of the surgical hub is higher than its threshold value. Based on at least the input received from one of the system modules and/or the modular device and the determination that one of the safety status level or the overload status level of the surgical hub is higher than its respective threshold, the surgical hub may determine a second control scheme to be configured and/or used to control the set of modules associated with the surgical hub. The second control scheme may be determined based on one or more of the needs of the surgical hub, priorities of the system modules and/or modular devices, and capacity of the system modules or modular devices, or capacity of the surgical hub.

The first control scheme or the second control scheme may be one of a cooperative control scheme, a notification control scheme, an antagonistic control scheme, or a hierarchical control scheme. The cooperative control scheme may include the surgical hub configuring the system modules and/or the modular devices to enable a first system module or a modular device to communicate with a second system module or the modular device such that a condition in the first system module or modular device impacts operation of the second system module or the modular device.

The notification control scheme may include the surgical hub enabling a first system module or the modular device to notify a second system module or modular device about an occurrence of an event or a parameter associated with one of the functions of the first system module or the modular device.

The antagonistic control scheme may include the surgical hub prioritizing a first task associated with a first system module or modular device over a second task associated with a second system module or modular device. The prioritization may be based on at least one of an importance of the module, a function of the first task, or a predefined configured value.

The hierarchical control scheme may include the surgical hub establishing a hierarchy of control between a first system module or modular device and a second system module or modular device.

The surgical hub may send a control program to one or more system modules and/or modular devices associated with the set of modules to establish the second control scheme. The surgical hub may determine the communication interfaces associated with the system modules and/or modular devices. The surgical hub may control the communication interfaces based on, for example, capabilities of the system modules and/or modular devices, interferences of the system modules and/or modular devices, and the data communicated by the system modules and/or modular devices. The surgical hub may identify configuration of a system module or a modular device using, for example, one of an electronic communication or a visualization using an operating room (OR) camera.

The surgical hub may adapt one of a communication limit, an interconnectivity, a master-slave control operation, a timing, or a data passing pathway based on the identified configuration of the one of the module, the equipment, or the device.

The surgical hub may identify configuration of the system module or the modular device based on a risk/harm database.

DETAILED DESCRIPTION

Figure 1A:
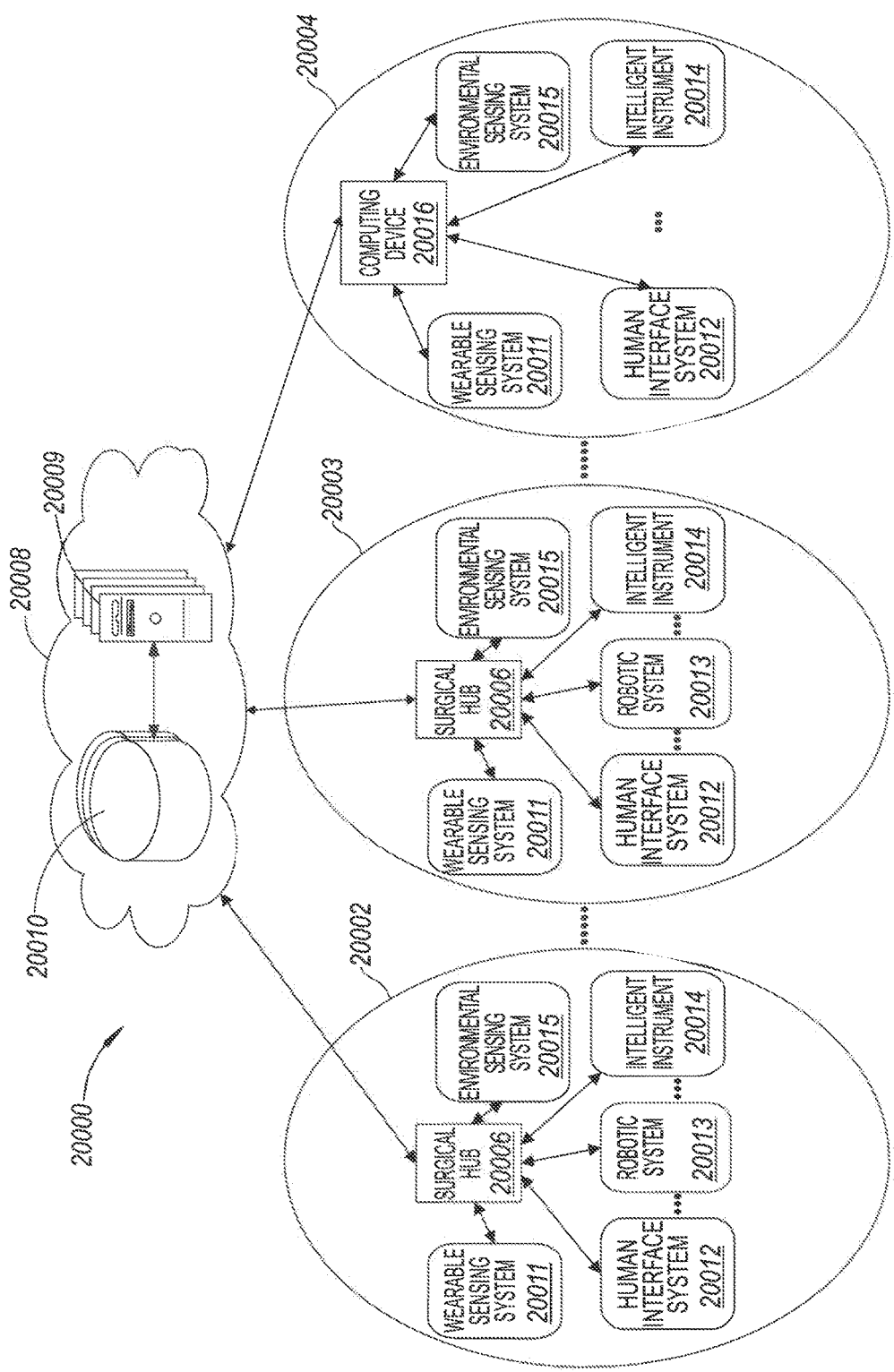
FIG. 1A is a block diagram of a computer-implemented surgical system.

FIG. 1A is a block diagram of a computer-implemented surgical system 20000. An example surgical system such as the surgical system 20000 may include one or more surgical systems (e.g., surgical sub-systems) 20002, 20003 and 20004. For example, surgical system 20002 may include a computer-implemented interactive surgical system. For example, surgical system 20002 may include a surgical hub 20006 and/or a computing device 20016 in communication with a cloud computing system 20008, for example, as described in FIG. 2. The cloud computing system 20008 may include at least one remote cloud server 20009 and at least one remote cloud storage unit 20010. Example surgical systems 20002, 20003, or 20004 may include a wearable sensing system 20011, an environmental sensing system 20015, a robotic system 20013, one or more intelligent instruments 20014, human interface system 20012, etc. The human interface system is also referred herein as the human interface device. The wearable sensing system 20011 may include one or more HCP sensing systems, and/or one or more patient sensing systems. The environmental sensing system 20015 may include one or more devices, for example, used for measuring one or more environmental attributes, for example, as further described in FIG. 2. The robotic system 20013 may include a plurality of devices used for performing a surgical procedure, for example, as further described in FIG. 2.

The surgical system 20002 may be in communication with a remote server 20009 that may be part of a cloud computing system 20008. In an example, the surgical system 20002 may be in communication with a remote server 20009 via an internet service provider's cable/FIOS networking node. In an example, a patient sensing system may be in direct communication with a remote server 20009. The surgical system 20002 and/or a component therein may communicate with the remote servers 20009 via a cellular transmission/reception point (TRP) or a base station using one or more of the following cellular protocols: GSM/GPRS/EDGE (2G), UMTS/HSPA (3G), long term evolution (LTE) or 4G, LTE-Advanced (LTE-A), new radio (NR) or 5G.

A surgical hub 20006 may have cooperative interactions with one of more means of displaying the image from the laparoscopic scope and information from one or more other smart devices and one or more sensing systems 20011. The surgical hub 20006 may interact with one or more sensing systems 20011, one or more smart devices, and multiple displays. The surgical hub 20006 may be configured to gather measurement data from the one or more sensing systems 20011 and send notifications or control messages to the one or more sensing systems 20011. The surgical hub 20006 may send and/or receive information including notification information to and/or from the human interface system 20012. The human interface system 20012 may include one or more human interface devices (HIDs). The surgical hub 20006 may send and/or receive notification information or control information to audio, display and/or control information to various devices that are in communication with the surgical hub.

For example, the sensing systems 20001 may include the wearable sensing system 20011 (which may include one or more HCP sensing systems and one or more patient sensing systems) and the environmental sensing system 20015 as discussed in FIG. 1A. The one or more sensing systems 20001 may measure data relating to various biomarkers. The one or more sensing systems 20001 may measure the biomarkers using one or more sensors, for example, photosensors (e.g., photodiodes, photoresistors), mechanical sensors (e.g., motion sensors), acoustic sensors, electrical sensors, electrochemical sensors, thermoelectric sensors, infrared sensors, etc. The one or more sensors may measure the biomarkers as described herein using one of more of the following sensing technologies: photoplethysmography, electrocardiography, electroencephalography, colorimetry, impedimentary, potentiometry, amperometry, etc.

The biomarkers measured by the one or more sensing systems 20001 may include, but are not limited to, sleep, core body temperature, maximal oxygen consumption, physical activity, alcohol consumption, respiration rate, oxygen saturation, blood pressure, blood sugar, heart rate variability, blood potential of hydrogen, hydration state, heart rate, skin conductance, peripheral temperature, tissue perfusion pressure, coughing and sneezing, gastrointestinal motility, gastrointestinal tract imaging, respiratory tract bacteria, edema, mental aspects, sweat, circulating tumor cells, autonomic tone, circadian rhythm, and/or menstrual cycle.

The biomarkers may relate to physiologic systems, which may include, but are not limited to, behavior and psychology, cardiovascular system, renal system, skin system, nervous system, gastrointestinal system, respiratory system, endocrine system, immune system, tumor, musculoskeletal system, and/or reproductive system. Information from the biomarkers may be determined and/or used by the computer-implemented patient and the surgical system 20000, for example. The information from the biomarkers may be determined and/or used by the computer-implemented patient and the surgical system 20000 to improve said systems and/or to improve patient outcomes, for example. The one or more sensing systems 20001, biomarkers 20005, and physiological systems are described in more detail in U.S. application Ser. No. 17/156,287, titled METHOD OF ADJUSTING A SURGICAL PARAMETER BASED ON BIOMARKER MEASUREMENTS, filed Jan. 22, 2021, the disclosure of which is herein incorporated by reference in its entirety.

Figure 1B:
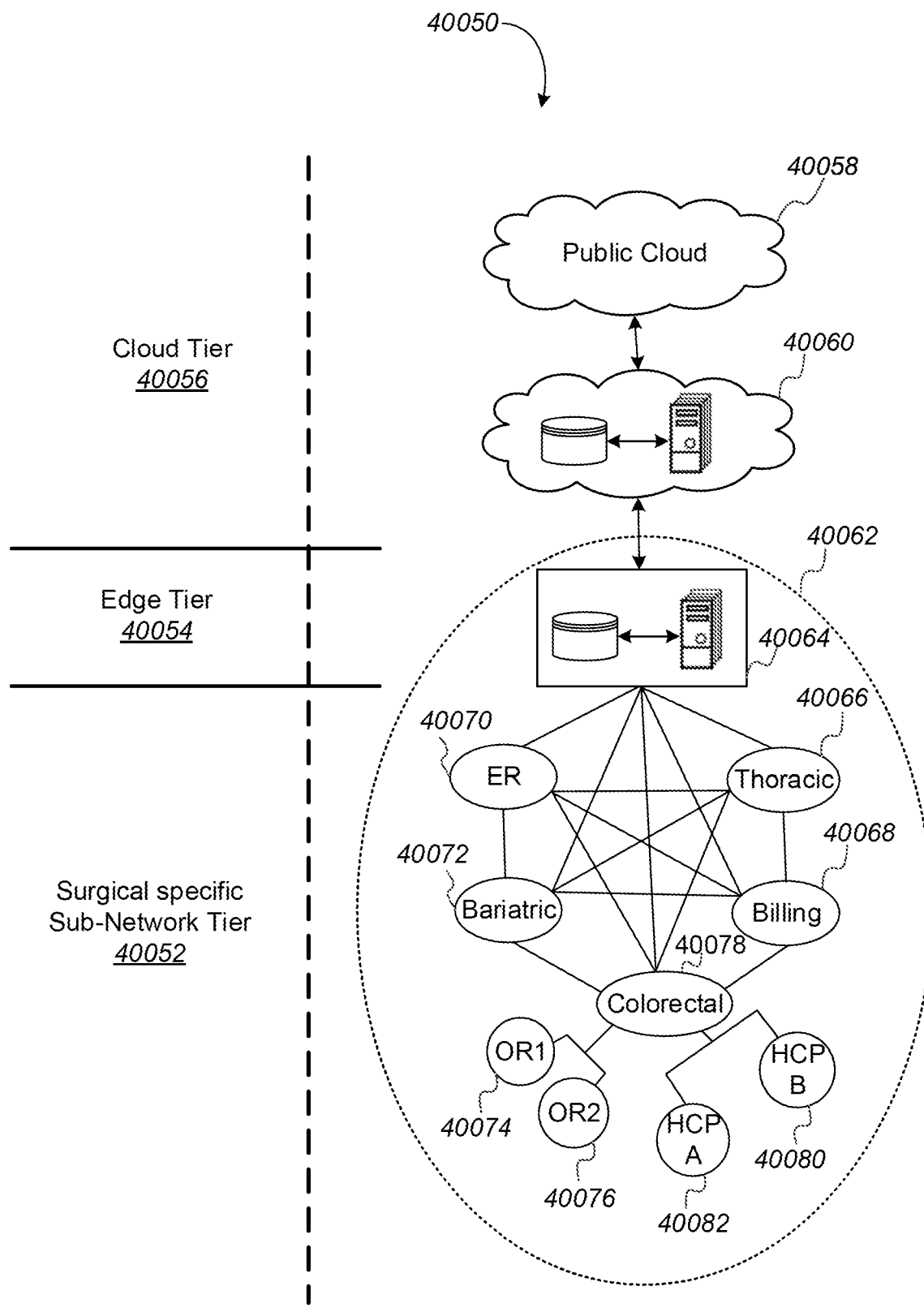
FIG. 1B is a block diagram of a computer-implemented multi-tier surgical system.

FIG. 1B is a block diagram of a computer-implemented multi-tier surgical system. As illustrated in FIG. 1B, a computer-implemented multi-tier surgical system 40050 may include multiple tiers of systems, such as a surgical specific sub-network tier system 40052, an edge tier system 40054 that is associated with the surgical specific sub-network tier system 40052, and a cloud tier system 40056.

A surgical specific sub-network tier system 40052 may include a plurality of inter-connected surgical sub-systems. For example, the surgical sub-systems may be grouped by the type of surgical procedures and/or other departments in a medical facility or a hospital. For example, a medical facility or a hospital may include a plurality of surgical procedure specific departments, such as an emergency room (ER) department 40070, colorectal department 40078, bariatric department 40072, thoracic department 40066, and billing department 40068. Each of the surgical procedure specific departments may include one or more surgical sub-systems associated with an operating room (OR) and/or a healthcare care professional (HCP). For example, the colorectal department 40078 may include a set of surgical hubs (e.g., surgical hub 20006 as described in FIG. 1A). The surgical hubs may be designated for a respective HCP, such as HCP A, 40082 and HCP B, 40080. In an example, the colorectal department may include a group of surgical hubs that may be located in respective ORs, such as OR1, 40074 and OR2, 40076. The medical facility or the hospital may also include a billing department subsystem 40068. The billing department subsystem 40068 may store and/or manage billing data associated with a respective department, such as the ER department 40070, colorectal department 40078, bariatric department 40072, and/or thoracic department 40066.

An edge tier system 40054 may be associated with a medical facility or a hospital and may include one or more edge computing systems 40064, for example. An edge computing system 40064 may include a storage sub-system and a server sub-system. In an example, the edge computing system comprising an edge server and/or a storage unit may provide additional processing and/or storage services to a surgical hub that is part of one of the departmental ORs (e.g., OR1 and OR2 of the colorectal department).

The surgical specific sub-network tier system 40052 and the edge tier system 40054 may be located within a Health Insurance Portability and Accountability Act (HIPAA) boundary 40062. The surgical specific sub-network system 40052 and the edge tier system 40054 may be connected to the same local data network. The local data network may be a local data network of a medical facility or a hospital. The local data network may be within the HIPAA boundary. Because the surgical specific sub-network tier system 40052 and the edge tier system 40054 are located within the HIPAA boundary 40062, patient data between an edge computing system 40064 and a device located within one of the entities of the surgical specific sub-network tier system 40052 may flow without redaction and/or encryption. For example, patient data between an edge computing system 40064 and a surgical hub located in OR1 40074 of the colorectal department 40078 may flow without redaction and/or encryption.

The cloud tier system 40056 may include an enterprise cloud system 40060 and a public cloud system 40058. For example, the enterprise cloud system 40060 may be a cloud computing system 20008 that includes a remote cloud server sub-system and/or a remote cloud storage subsystem, as described in FIG. 1A. The enterprise cloud system 40060 may be managed by an organization, such as a private company. The enterprise cloud system 40060 may be in communication with one or more entities (e.g., edge computing systems 40064, surgical hubs located in ORs (e.g., OR1 40074) of the various departments (e.g., colorectal department 40078)) that are located within the HIPAA boundary 40062.

The public cloud system 40058 may be operated by a cloud computing service provider. For example, the cloud computing service provider may provide storage services and/or computing services to a plurality of enterprise cloud systems (e.g., enterprise cloud system 40060).

Figure 1C:
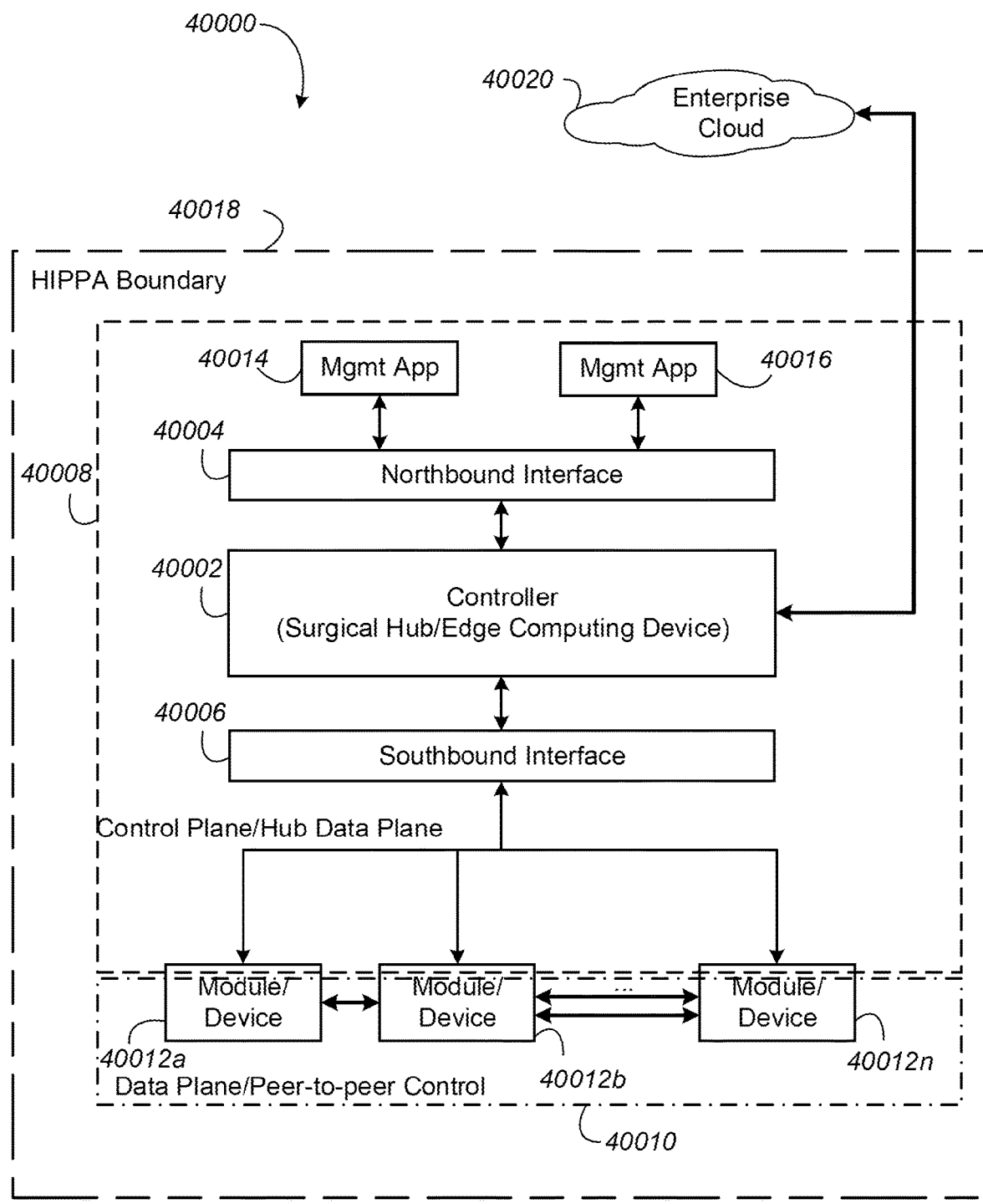
FIG. 1C is a logical diagram illustrating control plane and data plane of a surgical system.

FIG. 1C is a logical block diagram 40000 illustrating various communication planes in a surgical system. As illustrated in FIG. 1C, the communication planes between a controller 40002 and management applications 40014 and 40016 on one side and, the system modules and/or modular devices 40012a through 40012n on the other side, may use control plane 40008 and data plane 40010. In an example, in addition to the control plane 40008, a data plane may also exist between the system modules and/or modular devices 40012a through 40012n and the surgical hub. The data plane 40010 may provide data plane paths (e.g., redundant data plane paths) between the system modules and/or the modular devices 40012a through 40012n that are associated with one or more surgical hubs. A surgical hub or one of the surgical hubs (e.g., in case of a plurality of surgical hubs present in an operating room) may act as a controller 40002. In an example, the controller 40002 may be an edge computing system that may reside within a Health Insurance Portability and Accountability Act (HIPAA) boundary where the surgical system is located, for example, as illustrated in FIG. 1B. The controller 40002 may be in communication with an enterprise cloud system 40020. As illustrated in FIG. 1C, the enterprise cloud system 40020 may be located outside the HIPAA boundary 40018. Accordingly, the patient data flowing to and/or from the enterprise cloud system 40020 may be redacted and/or encrypted.

The controller 40002 may be configured to provide a northbound interface 40004 and a southbound interface 40006. The northbound interface 40004 may be used for providing a control plane 40008. The control plane 40008 may include one or more management applications 40014 and 40016 that may enable a user to configure and/or manage system modules and/or modular devices modular devices 40012a through 40012n associated with a surgical system. The management applications 40014 and 40016 may be used to obtain status of various system modules and/or the modular devices 40012a through 40012n.

The management applications 40014 and 40016 using the control plane may interact with the controller 40002, for example, using a set of application programming interface (API) calls. The management applications 40014 and 40016 may interact with the controller 40002 via a management protocol or an application layer protocol to configure and/or monitor the status of a system module and/or a modular device. The management protocols or the application layer protocols used to monitor the status and/or configure a system module or a modular device associated with a surgical system may include the simple network management protocol (SNMP), TELNET protocol, secure shell (SSH) protocol, network configuration protocol (NETCONF), etc.

SNMP or a similar protocol may be used to collect status information and/or send configuration related data (e.g., configuration related control programs) associated with system modules and/or modular devices to the controller. SNMP or a similar protocol may collect information by selecting devices associated with a surgical system from a central network management console using messages (e.g., SNMP messages). The messages may be sent and/or received at fixed or random intervals. The messages may include Get messages and Set messages. The Get messages or messages similar to the Get messages may be used for obtaining information from a system module or a modular device associated with a surgical system. The Set message or messages similar to the Set message may be used for changing a configuration associated with a system module or a modular device associated with a surgical system.

For example, the Get messages or similar messages may include the SNMP messages GetRequest, GetNextRequest, or GetBulkRequest. The Set messages may include SNMP SetRequest message. The GetRequest, GetNextRequest, GetBulkRequest messages or similar messages may be used by a configuration manager (e.g., an SNMP manager) running on the controller 40002. The configuration manager may be in communication with a communication agent (e.g., an SNMP agent) that may be a part of a system module and/or a modular device in a surgical system. The SNMP message SetRequest message or similar may be used by the communication manager on the controller 40002 to set the value of a parameter or an object instance in the communication agent on a system module and/or a modular device of a surgical system. In an example, SNMP modules, for example, may be used to establish communication path between system modules and/or modular devices associated with a surgical system.

Based on the query or configuration related messages received from a management application, such as management applications 40014 and 40016, the controller 40002 may generate configuration queries and/or configuration data for querying or configuring the system modules and/or the modular devices associated with the surgical hub or the surgical system. A surgical hub (e.g., the surgical hub 20006 shown in FIG. 1A) or an edge computing system (e.g., the edge computing system 40064 shown in FIG. 1B) may manage and/or control various system modules and/or modular devices 40012*a* through 40012*n* associated with a surgical system. For example, the northbound interface 40004 of the controller 40002 may be used for changing control interactions between one or more modules associated and/or devices associated with a surgical system. In an example, the controller 40002 may be used for establishing one or more communication data paths between a plurality of modules and/or devices associated with a surgical system. The controller 40002 may use its southbound interface 40006 to send the control programs comprising queries and/or configuration changes to the system modules and/or the modular devices of the surgical system.

The system modules and/or the modular devices 40012*a* through 40012*n* of a surgical system, or the communication agents that may be a part of the system modules and/or the modular devices, may send notification messages or traps to the controller 40002. The controller may forward the notification messages or traps via its northbound interface 40004 to the management application 40014 and 40016 for displaying on a display. In an example, the controller 40002 may send the notification to other system modules and/or modular devices 40012*a* through 40012*n* that are part of the surgical system.

The system modules and/or the modular devices 40012*a* through 40012*n* of a surgical system or the communication agents that are part of the system modules and/or the modular devices may send responses to the queries received from the controller 40002. For example, a communication agent that may be part of a system module or a modular device may send a response message in response to a Get or a Set message or messages similar to the Get or the Set messages received from the controller 40002. In an example, in response to a Get message or a similar message received from the controller 40002, the response message from the system module or the modular device 40012*a* through 40012*n* may include the data requested. In an example, in response to a Set message or a similar message received from a system module or a modular device 40012*a* through 40012*n*, the response message from the controller 40002 may include the newly set value as confirmation that the value has been set.

A trap or a notification message or a message similar to the trap or the notification message may be used by a system module or a modular device 40012*a* through 40012*n* to provide information about events associated with the system modules or the modular devices. For example, a trap or a notification message may be sent from a system module or a modular device 40012*a* through 40012*n* to the controller 40002 indicating a status of a communication interface (e.g., whether it available or unavailable for communication). The controller 40002 may send a receipt of the trap message back to the system module or the modular device 40012*a* through 40012*n* (e.g., to the agent on the system module or a modular device).

In an example, TELNET protocol may be used to provide a bidirectional interactive text-oriented communication facility between system modules and/or modular devices 40012*a* through 40012*n* and the controller 40002. TELNET protocol may be used to collect status information and/or send configuration data (e.g., control programs) from/to the controller 40002. TELNET may be used by one of the management applications 40014 or 40016 to establish a connection with the controller 40002 using the transmission control protocol port number 23.

In an example, SSH, a cryptographic encrypted protocol, may be used to allow remote login and to collect status information and/or send configuration data about system modules and/or modular devices 40012*a* through 40012*n* from/to the controller 40002. SSH may be used by one of the management applications 40014 or 40016 to establish an encrypted connection with the controller 40002 using the transmission control protocol port number 22.

In an example, NETCONF may be used to perform management functions by invoking remote procedure calls using, for example, <rpc>, <rpc-reply>, or <edit-config> operations. The <rpc> and <rpc-reply> procedure calls or similar procedure calls may be used for exchanging information from a system module and/or a modular device associated with a surgical system. The NETCONF<edit-config> operation or a similar operation may be used for configuring the system modules and/or the modular devices associated with the surgical system.

The controller 40002 may configure the system modules and/or modular device 40012*a* through 40012*n* to establish a data plane 40010. The data plane 40010 (e.g., also referred to as a user plane or a forwarding plane) may enable a communication data path between a plurality of system modules and/or modular device 40012*a* through 40012*n*. The data plane 40010 may be utilized by the system modules and/or the modular device 40012*a* through 40012*n* for communicating data flows of data between the system modules and/or modular devices associated with a surgical system. The data flows may be established using one or more dedicated communication interfaces between the system modules and/or the modular devices associated with one or more surgical hubs of a surgical system. In an example, the data flows may be established over one or more local area networks (LANs) and one or more wide area networks (WANs), such as the Internet.

In an example, the data plane 40010 may provide support for establishing a first and a second independent, disjointed, concurrent, and redundant communication path for data flow between the system modules and/or modular devices 40012*b* and 40012*n*. As illustrated in FIG. 1C. redundant communication paths may be established between system modules/modular devices 40012*b* and 40012*n*. The redundant communication paths may carry same/redundant data flows between the system modules and/or modular devices. In an example, when or if some of the data packets are dropped on one of the redundant communication paths due to problems with one of the communication interfaces on the system modules/modular devices 40012*b* and 40012*n*, the system modules and/or the modular devices may continue to send/receive at least one copy of the dropped data packets over the second communication path.

Figure 2:
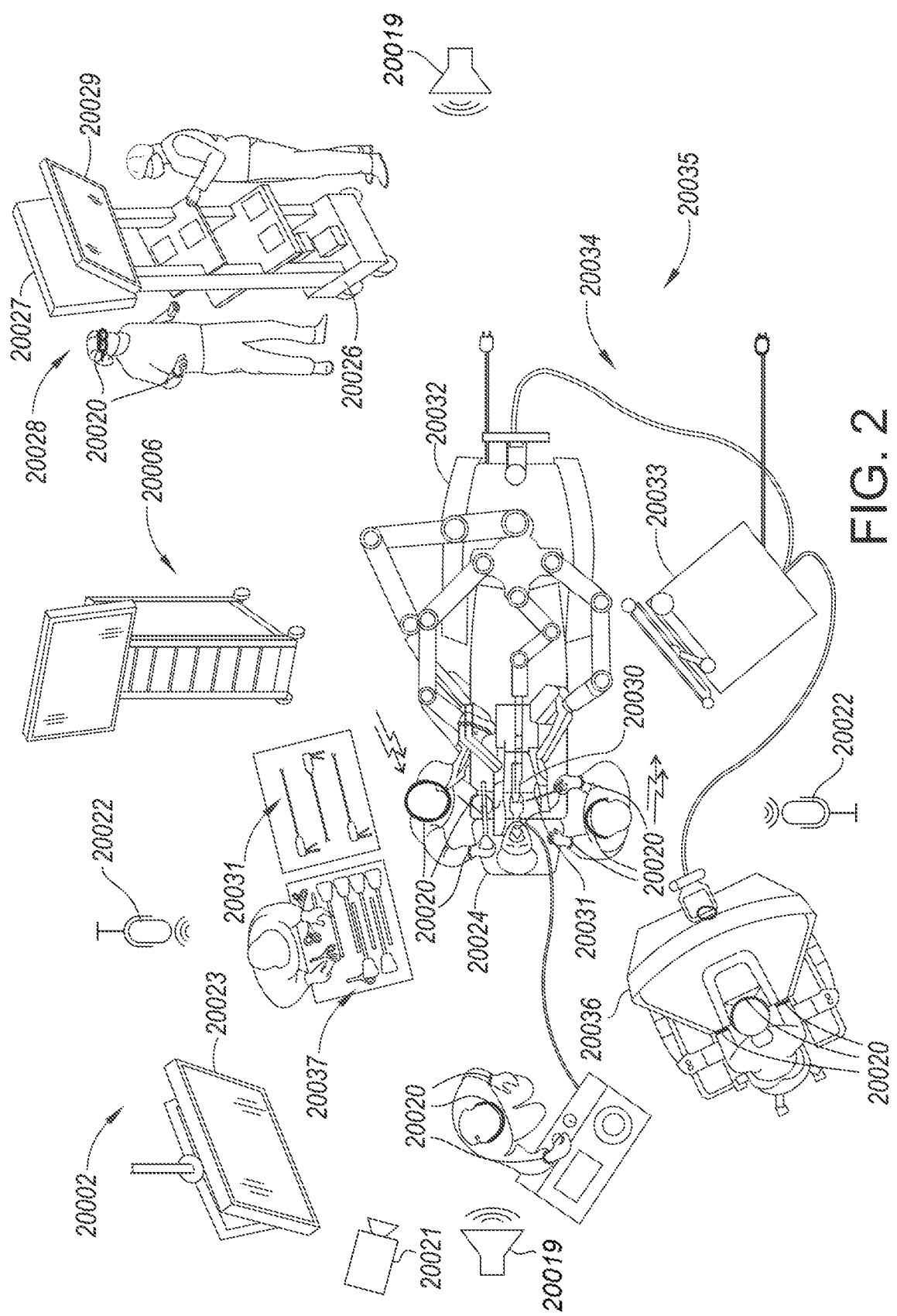
FIG. 2 shows an example surgical system in a surgical operating room.

FIG. 2 shows an example of a surgical system 20002 in a surgical operating room. As illustrated in FIG. 2, a patient is being operated on by one or more health care professionals (HCPs). The HCPs are being monitored by one or more HCP sensing systems 20020 worn by the HCPs. The HCPs and the environment surrounding the HCPs may also be monitored by one or more environmental sensing systems including, for example, a set of cameras 20021, a set of microphones 20022, and other sensors that may be deployed in the operating room. The HCP sensing systems 20020 and the environmental sensing systems may be in communication with a surgical hub 20006, which in turn may be in communication with one or more cloud servers 20009 of the cloud computing system 20008, as shown in FIG. 1A. The environmental sensing systems may be used for measuring one or more environmental attributes, for example, HCP position in the surgical theater, HCP movements, ambient noise in the surgical theater, temperature/humidity in the surgical theater, etc.

As illustrated in FIG. 2, a primary display 20023 and one or more audio output devices (e.g., speakers 20019) are positioned in the sterile field to be visible to an operator at the operating table 20024. In addition, a visualization/notification tower 20026 is positioned outside the sterile field. The visualization/notification tower 20026 may include a first non-sterile human interactive device (HID) 20027 and a second non-sterile HID 20029, which may face away from each other. The HID may be a display or a display with a touchscreen allowing a human to interface directly with the HID. A human interface system, guided by the surgical hub 20006, may be configured to utilize the HIDs 20027, 20029, and 20023 to coordinate information flow to operators inside and outside the sterile field. In an example, the surgical hub 20006 may cause an HID (e.g., the primary HID 20023) to display a notification and/or information about the patient and/or a surgical procedure step. In an example, the surgical hub 20006 may prompt for and/or receive input from personnel in the sterile field or in the non-sterile area. In an example, the surgical hub 20006 may cause an HID to display a snapshot of a surgical site, as recorded by an imaging device 20030, on a non-sterile HID 20027 or 20029, while maintaining a live feed of the surgical site on the primary HID 20023. The snapshot on the non-sterile display 20027 or 20029 can permit a non-sterile operator to perform a diagnostic step relevant to the surgical procedure, for example.

In one aspect, the surgical hub 20006 may be configured to route a diagnostic input or feedback entered by a non-sterile operator at the visualization tower 20026 to the primary display 20023 within the sterile field, where it can be viewed by a sterile operator at the operating table. In one example, the input can be in the form of a modification to the snapshot displayed on the non-sterile display 20027 or 20029, which can be routed to the primary display 20023 by the surgical hub 20006.

Referring to FIG. 2, a surgical instrument 20031 is being used in the surgical procedure as part of the surgical system 20002. The hub 20006 may be configured to coordinate information flow to a display of the surgical instrument 20031. For example, in U.S. Patent Application Publication No. US 2019-0200844 A1 (U.S. patent application Ser. No. 16/209,385), titled METHOD OF HUB COMMUNICATION, PROCESSING, STORAGE AND DISPLAY, filed Dec. 4, 2018, the disclosure of which is herein incorporated by reference in its entirety. A diagnostic input or feedback entered by a non-sterile operator at the visualization tower 20026 can be routed by the hub 20006 to the surgical instrument display within the sterile field, where it can be viewed by the operator of the surgical instrument 20031. Example surgical instruments that are suitable for use with the surgical system 20002 are described under the heading "Surgical Instrument Hardware" and in U.S. Patent Application Publication No. US 2019-0200844 A1 (U.S. patent application Ser. No. 16/209,385), titled METHOD OF HUB COMMUNICATION, PROCESSING, STORAGE AND DISPLAY, filed Dec. 4, 2018, the disclosure of which is herein incorporated by reference in its entirety, for example.

FIG. 2 illustrates an example of a surgical system 20002 being used to perform a surgical procedure on a patient who is lying down on an operating table 20024 in a surgical operating room 20035. A robotic system 20034 may be used in the surgical procedure as a part of the surgical system 20002. The robotic system 20034 may include a surgeon's console 20036, a patient side cart 20032 (surgical robot), and a surgical robotic hub 20033. The patient side cart 20032 can manipulate at least one removably coupled surgical tool 20037 through a minimally invasive incision in the body of the patient while the surgeon views the surgical site through the surgeon's console 20036. An image of the surgical site can be obtained by a medical imaging device 20030, which can be manipulated by the patient side cart 20032 to orient the imaging device 20030. The robotic hub 20033 can be used to process the images of the surgical site for subsequent display to the surgeon through the surgeon's console 20036.

Other types of robotic systems can be readily adapted for use with the surgical system 20002. Various examples of robotic systems and surgical tools that are suitable for use with the present disclosure are described in U.S. Patent Application Publication No. US 2019-0201137 A1 (U.S. patent application Ser. No. 16/209,407), titled METHOD OF ROBOTIC HUB COMMUNICATION, DETECTION, AND CONTROL, filed Dec. 4, 2018, the disclosure of which is herein incorporated by reference in its entirety.

Various examples of cloud-based analytics that are performed by the cloud computing system 20008, and are suitable for use with the present disclosure, are described in U.S. Patent Application Publication No. US 2019-0206569 A1 (U.S. patent application Ser. No. 16/209,403), titled METHOD OF CLOUD BASED DATA ANALYTICS FOR USE WITH THE HUB, filed Dec. 4, 2018, the disclosure of which is herein incorporated by reference in its entirety.

In various aspects, the imaging device 20030 may include at least one image sensor and one or more optical components. Suitable image sensors may include, but are not limited to, Charge-Coupled Device (CCD) sensors and Complementary Metal-Oxide Semiconductor (CMOS) sensors.

The optical components of the imaging device 20030 may include one or more illumination sources and/or one or more lenses. The one or more illumination sources may be directed to illuminate portions of the surgical field. The one or more image sensors may receive light reflected or refracted from the surgical field, including light reflected or refracted from tissue and/or surgical instruments.

The one or more illumination sources may be configured to radiate electromagnetic energy in the visible spectrum as well as the invisible spectrum. The visible spectrum, sometimes referred to as the optical spectrum or luminous spectrum, is the portion of the electromagnetic spectrum that is visible to (i.e., can be detected by) the human eye and may be referred to as visible light or simply light. A typical human eye will respond to wavelengths in air that range from about 380 nm to about 750 nm.

The invisible spectrum (e.g., the non-luminous spectrum) is the portion of the electromagnetic spectrum that lies below and above the visible spectrum (i.e., wavelengths below about 380 nm and above about 750 nm). The invisible spectrum is not detectable by the human eye. Wavelengths greater than about 750 nm are longer than the red visible spectrum, and they become invisible infrared (IR), microwave, and radio electromagnetic radiation. Wavelengths less than about 380 nm are shorter than the violet spectrum, and they become invisible ultraviolet, x-ray, and gamma ray electromagnetic radiation.

In various aspects, the imaging device 20030 is configured for use in a minimally invasive procedure. Examples of imaging devices suitable for use with the present disclosure include, but are not limited to, an arthroscope, angioscope, bronchoscope, choledochoscope, colonoscope, cytoscope, duodenoscope, enteroscope, esophagogastro-duodenoscope (gastroscope), endoscope, laryngoscope, nasopharyngo-neproscope, sigmoidoscope, thoracoscope, and ureteroscope.

The imaging device may employ multi-spectrum monitoring to discriminate topography and underlying structures. A multi-spectral image is one that captures image data within specific wavelength ranges across the electromagnetic spectrum. The wavelengths may be separated by filters or by the use of instruments that are sensitive to particular wavelengths, including light from frequencies beyond the visible light range, e.g., IR and ultraviolet. Spectral imaging can allow extraction of additional information that the human eye fails to capture with its receptors for red, green, and blue. The use of multi-spectral imaging is described in greater detail under the heading "Advanced Imaging Acquisition Module" in U.S. Patent Application Publication No. US 2019-0200844 A1 (U.S. patent application Ser. No. 16/209,385), titled METHOD OF HUB COMMUNICATION, PROCESSING, STORAGE AND DISPLAY, filed Dec. 4, 2018, the disclosure of which is herein incorporated by reference in its entirety. Multi-spectrum monitoring can be a useful tool in relocating a surgical field after a surgical task is completed to perform one or more of the previously described tests on the treated tissue. It is axiomatic that strict sterilization of the operating room and surgical equipment is required during any surgery. The strict hygiene and sterilization conditions required in a "surgical theater," i.e., an operating or treatment room, necessitate the highest possible sterility of all medical devices and equipment. Part of that sterilization process is the need to sterilize anything that comes in contact with the patient or penetrates the sterile field, including the imaging device 20030 and its attachments and components. It will be appreciated that the sterile field may be considered a specified area, such as within a tray or on a sterile towel, that is considered free of microorganisms, or the sterile field may be considered an area, immediately around a patient, who has been prepared for a surgical procedure. The sterile field may include the scrubbed team members, who are properly attired, and all furniture and fixtures in the area.

Wearable sensing system 20011 illustrated in FIG. 1A may include one or more sensing systems, for example, HCP sensing systems 20020 as shown in FIG. 2. The HCP sensing systems 20020 may include sensing systems to monitor and detect a set of physical states and/or a set of physiological states of a healthcare personnel (HCP). An HCP may be a surgeon or one or more healthcare personnel assisting the surgeon or other healthcare service providers in general. In an example, a sensing system 20020 may measure a set of biomarkers to monitor the heart rate of an HCP. In an example, a sensing system 20020 worn on a surgeon's wrist (e.g., a watch or a wristband) may use an accelerometer to detect hand motion and/or shakes and determine the magnitude and frequency of tremors. The sensing system 20020 may send the measurement data associated with the set of biomarkers and the data associated with a physical state of the surgeon to the surgical hub 20006 for further processing. One or more environmental sensing devices may send environmental information to the surgical hub 20006. For example, the environmental sensing devices may include a camera 20021 for detecting hand/body position of an HCP. The environmental sensing devices may include microphones 20022 for measuring the ambient noise in the surgical theater. Other environmental sensing devices may include devices, for example, a thermometer to measure temperature and a hygrometer to measure humidity of the surroundings in the surgical theater, etc. The surgical hub 20006, alone or in communication with the cloud computing system, may use the surgeon biomarker measurement data and/or environmental sensing information to modify the control algorithms of hand-held instruments or the averaging delay of a robotic interface, for example, to minimize tremors. In an example, the HCP sensing systems 20020 may measure one or more surgeon biomarkers associated with an HCP and send the measurement data associated with the surgeon biomarkers to the surgical hub 20006. The HCP sensing systems 20020 may use one or more of the following RF protocols for communicating with the surgical hub 20006: Bluetooth, Bluetooth Low-Energy (BLE), Bluetooth Smart, Zigbee, Z-wave, IPv6 Low-power wireless Personal Area Network (6LoWPAN), Wi-Fi. The surgeon biomarkers may include one or more of the following: stress, heart rate, etc. The environmental measurements from the surgical theater may include ambient noise level associated with the surgeon or the patient, surgeon and/or staff movements, surgeon and/or staff attention level, etc.

The surgical hub 20006 may use the surgeon biomarker measurement data associated with an HCP to adaptively control one or more surgical instruments 20031. For example, the surgical hub 20006 may send a control program to a surgical instrument 20031 to control its actuators to limit or compensate for fatigue and use of fine motor skills. The surgical hub 20006 may send the control program based on situational awareness and/or the context on importance or criticality of a task. The control program may instruct the instrument to alter operation to provide more control when control is needed.

Figure 3:
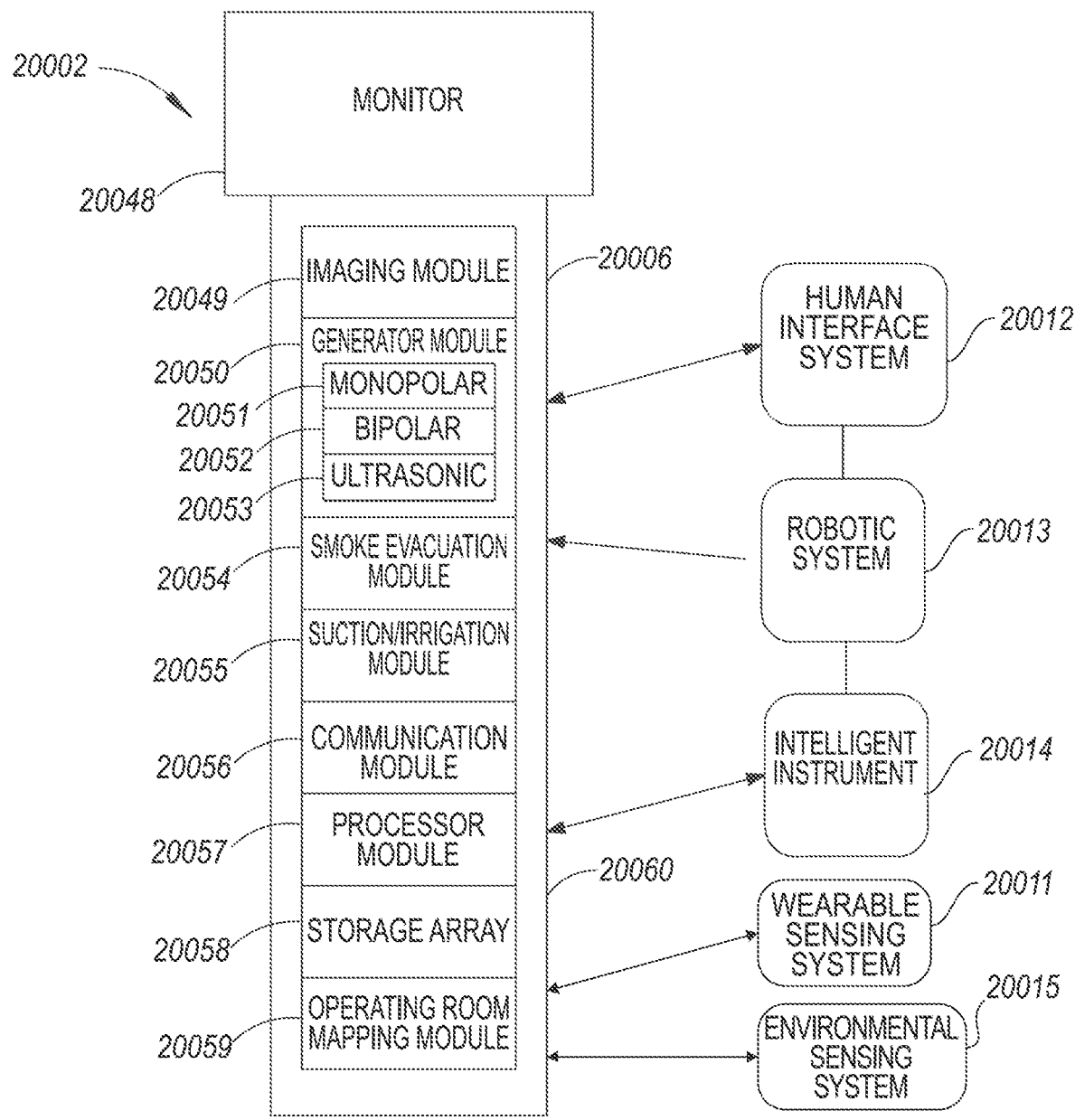
FIG. 3 illustrates an example surgical hub paired with various systems.

FIG. 3 shows an example surgical system 20002 with a surgical hub 20006 paired with a wearable sensing system 20011, an environmental sensing system 20015, a human interface system 20012, a robotic system 20013, and an intelligent instrument 20014. The hub 20006 includes a display 20048, an imaging module 20049, a generator module 20050, a communication module 20056, a processor module 20057, a storage array 20058, and an operating-room mapping module 20059. In certain aspects, as illustrated in FIG. 3, the hub 20006 further includes a smoke evacuation module 20054 and/or a suction/irrigation module 20055. During a surgical procedure, energy application to tissue, for sealing and/or cutting, is generally associated with smoke evacuation, suction of excess fluid, and/or irrigation of the tissue. Fluid, power, and/or data lines from different sources are often entangled during the surgical procedure. Valuable time can be lost addressing this issue during a surgical procedure. Detangling the lines may necessitate disconnecting the lines from their respective modules, which may require resetting the modules. The hub modular enclosure 20060 offers a unified environment for managing the power, data, and fluid lines, which reduces the frequency of entanglement between such lines. Aspects of the present disclosure present a surgical hub 20006 for use in a surgical procedure that involves energy application to tissue at a surgical site. The surgical hub 20006 includes a hub enclosure 20060 and a combo generator module slidably receivable in a docking station of the hub enclosure 20060. The docking station includes data and power contacts. The combo generator module includes two or more of an ultrasonic energy generator component, a bipolar RF energy generator component, and a monopolar RF energy generator component that are housed in a single unit. In one aspect, the combo generator module also includes a smoke evacuation component, at least one energy delivery cable for connecting the combo generator module to a surgical instrument, at least one smoke evacuation component configured to evacuate smoke, fluid, and/or particulates generated by the application of therapeutic energy to the tissue, and a fluid line extending from the remote surgical site to the smoke evacuation component. In one aspect, the fluid line may be a first fluid line, and a second fluid line may extend from the remote surgical site to a suction and irrigation module 20055 slidably received in the hub enclosure 20060. In one aspect, the hub enclosure 20060 may include a fluid interface. Certain surgical procedures may require the application of more than one energy type to the tissue. One energy type may be more beneficial for cutting the tissue, while another different energy type may be more beneficial for sealing the tissue. For example, a bipolar generator can be used to seal the tissue while an ultrasonic generator can be used to cut the sealed tissue. Aspects of the present disclosure present a solution where a hub modular enclosure 20060 is configured to accommodate different generators and facilitate an interactive communication therebetween. One of the advantages of the hub modular enclosure 20060 is enabling the quick removal and/or replacement of various modules. Aspects of the present disclosure present a modular surgical enclosure for use in a surgical procedure that involves energy application to tissue. The modular surgical enclosure includes a first energy-generator module, configured to generate a first energy for application to the tissue, and a first docking station comprising a first docking port that includes first data and power contacts, wherein the first energy-generator module is slidably movable into an electrical engagement with the power and data contacts and wherein the first energy-generator module is slidably movable out of the electrical engagement with the first power and data contacts. Further to the above, the modular surgical enclosure also includes a second energy-generator module configured to generate a second energy, different than the first energy, for application to the tissue, and a second docking station comprising a second docking port that includes second data and power contacts, wherein the second energy generator module is slidably movable into an electrical engagement with the power and data contacts, and wherein the second energy-generator module is slidably movable out of the electrical engagement with the second power and data contacts. In addition, the modular surgical enclosure also includes a communication bus between the first docking port and the second docking port, configured to facilitate communication between the first energy-generator module and the second energy-generator module. Referring to FIG. 3, aspects of the present disclosure are presented for a hub modular enclosure 20060 that allows the modular integration of a generator module 20050, a smoke evacuation module 20054, and a suction/irrigation module 20055. The hub modular enclosure 20060 further facilitates interactive communication between the modules 20059, 20054, and 20055. The generator module 20050 can be with integrated monopolar, bipolar, and ultrasonic components supported in a single housing unit slidably insertable into the hub modular enclosure 20060. The generator module 20050 can be configured to connect to a monopolar device 20051, a bipolar device 20052, and an ultrasonic device 20053. Alternatively, the generator module 20050 may comprise a series of monopolar, bipolar, and/or ultrasonic generator modules that interact through the hub modular enclosure 20060. The hub modular enclosure 20060 can be configured to facilitate the insertion of multiple generators and interactive communication between the generators docked into the hub modular enclosure 20060 so that the generators would act as a single generator.

Figure 4:
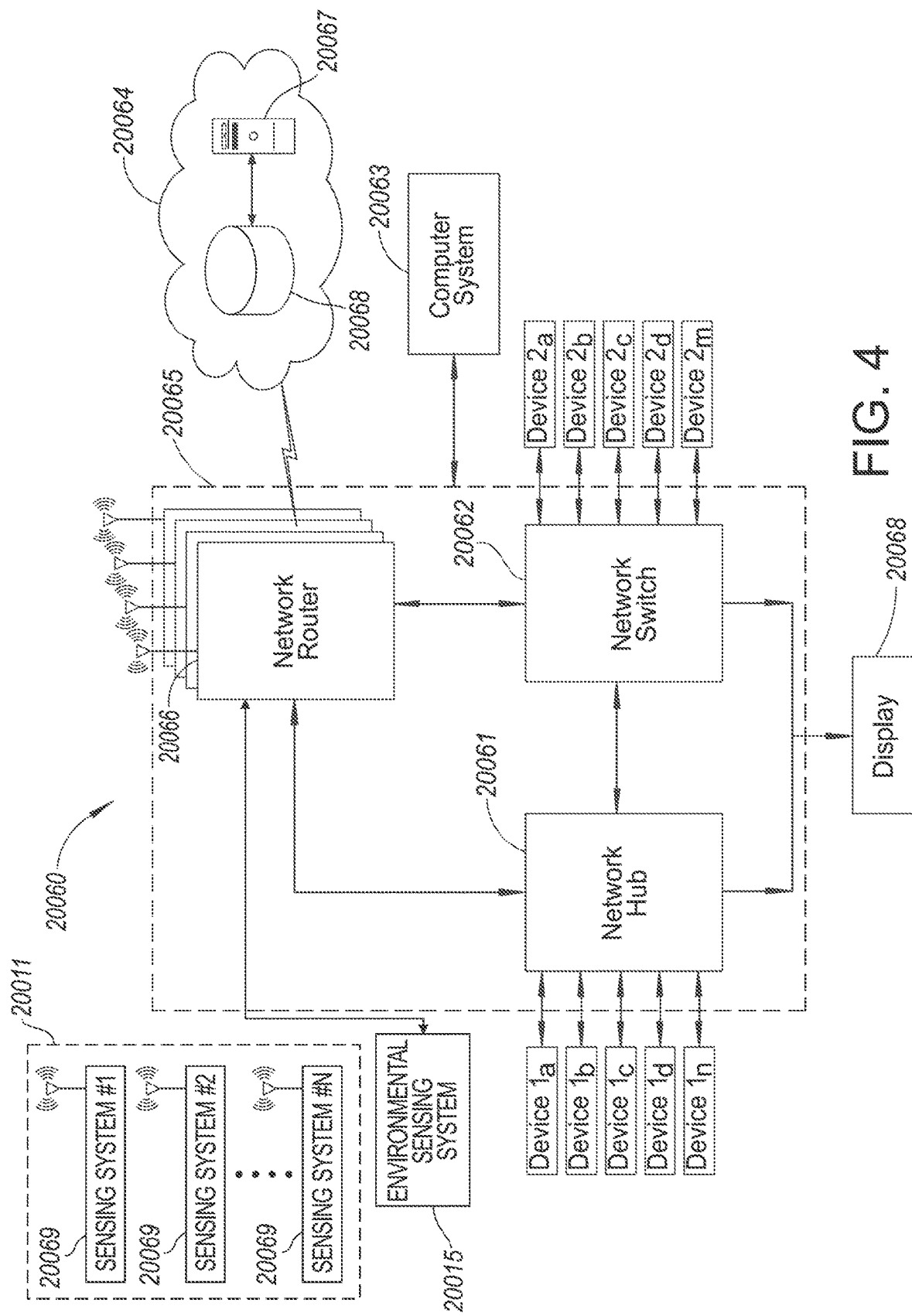
FIG. 4 illustrates a surgical data network having a set of communication surgical hubs configured to connect with a set of sensing systems, an environmental sensing system, a set of devices, etc.

FIG. 4 illustrates a surgical data network having a set of communication hubs configured to connect a set of sensing systems, environment sensing system(s), and a set of other modular devices located in one or more operating theaters of a healthcare facility, a patient recovery room, or a room in a healthcare facility specially equipped for surgical operations, to the cloud, in accordance with at least one aspect of the present disclosure.

As illustrated in FIG. 4, a surgical hub system 20060 may include a modular communication hub 20065 that is configured to connect modular devices located in a healthcare facility to a cloud-based system (e.g., a cloud computing system 20064 that may include a remote server 20067 coupled to a remote storage 20068). The modular communication hub 20065 and the devices may be connected in a room in a healthcare facility specially equipped for surgical operations. In one aspect, the modular communication hub 20065 may include a network hub 20061 and/or a network switch 20062 in communication with a network router 20066. The modular communication hub 20065 may be coupled to a local computer system 20063 to provide local computer processing and data manipulation.

The computer system 20063 may comprise a processor and a network interface 20100. The processor may be coupled to a communication module, storage, memory, non-volatile memory, and input/output (I/O) interface via a system bus. The system bus can be any of several types of bus structure(s) including the memory bus or memory controller, a peripheral bus or external bus, and/or a local bus using any variety of available bus architectures including, but not limited to, 9-bit bus, Industrial Standard Architecture (ISA), Micro-Charnel Architecture (MSA), Extended ISA (EISA), Intelligent Drive Electronics (IDE), VESA Local Bus (VLB), Peripheral Component Interconnect (PCI), USB, Advanced Graphics Port (AGP), Personal Computer Memory Card International Association bus (PCMCIA), Small Computer Systems Interface (SCSI), or any other proprietary bus.

The processor may be any single-core or multicore processor such as those known under the trade name ARM Cortex by Texas Instruments. In one aspect, the processor may be an LM4F230H5QR ARM Cortex-M4F Processor Core, available from Texas Instruments, for example, comprising an on-chip memory of 256 KB single-cycle flash memory, or other non-volatile memory, up to 40 MHz, a prefetch buffer to improve performance above 40 MHz, a 32 KB single-cycle serial random access memory (SRAM), an internal read-only memory (ROM) loaded with StellarisWare® software, a 2 KB electrically erasable programmable read-only memory (EEPROM), and/or one or more pulse width modulation (PWM) modules, one or more quadrature encoder inputs (QEI) analogs, one or more 12-bit analog-to-digital converters (ADCs) with 12 analog input channels, details of which are available for the product datasheet.

In an example, the processor may comprise a safety controller comprising two controller-based families such as TMS570 and RM4x, known under the trade name Hercules ARM Cortex R4, also by Texas Instruments. The safety controller may be configured specifically for IEC 61508 and ISO 26262 safety critical applications, among others, to provide advanced integrated safety features while delivering scalable performance, connectivity, and memory options.

It is to be appreciated that the computer system 20063 may include software that acts as an intermediary between users and the basic computer resources described in a suitable operating environment. Such software may include an operating system. The operating system, which can be stored on the disk storage, may act to control and allocate resources of the computer system. System applications may take advantage of the management of resources by the operating system through program modules and program data stored either in the system memory or on the disk storage. It is to be appreciated that various components described herein can be implemented with various operating systems or combinations of operating systems.

A user may enter commands or information into the computer system 20063 through input device(s) coupled to the I/O interface. The input devices may include, but are not limited to, a pointing device such as a mouse, trackball, stylus, touch pad, keyboard, microphone, joystick, game pad, satellite dish, scanner, TV tuner card, digital camera, digital video camera, web camera, and the like. These and other input devices connect to the processor 20102 through the system bus via interface port(s). The interface port(s) include, for example, a serial port, a parallel port, a game port, and a USB. The output device(s) use some of the same types of ports as input device(s). Thus, for example, a USB port may be used to provide input to the computer system 20063 and to output information from the computer system 20063 to an output device. An output adapter may be provided to illustrate that there can be some output devices like monitors, displays, speakers, and printers, among other output devices that may require special adapters. The output adapters may include, by way of illustration and not limitation, video and sound cards that provide a means of connection between the output device and the system bus. It should be noted that other devices and/or systems of devices, such as remote computer(s), may provide both input and output capabilities.

The computer system 20063 can operate in a networked environment using logical connections to one or more remote computers, such as cloud computer(s), or local computers. The remote cloud computer(s) can be a personal computer, server, router, network PC, workstation, microprocessor-based appliance, peer device, or other common network node, and the like, and typically includes many or all of the elements described relative to the computer system. For purposes of brevity, only a memory storage device is illustrated with the remote computer(s). The remote computer(s) may be logically connected to the computer system through a network interface and then physically connected via a communication connection. The network interface may encompass communication networks such as local area networks (LANs) and wide area networks (WANs). LAN technologies may include Fiber Distributed Data Interface (FDDI), Copper Distributed Data Interface (CDDI), Ethernet/IEEE 802.3, Token Ring/IEEE 802.5, and the like. WAN technologies may include, but are not limited to, point-to-point links, circuit-switching networks like Integrated Services Digital Networks (ISDN) and variations thereon, packet-switching networks, and Digital Subscriber Lines (DSL).

In various examples, the computer system 20063 may comprise an image processor, image-processing engine, media processor, or any specialized digital signal processor (DSP) used for the processing of digital images. The image processor may employ parallel computing with single instruction, multiple data (SIMD) or multiple instruction, multiple data (MIMD) technologies to increase speed and efficiency. The digital image-processing engine can perform a range of tasks. The image processor may be a system on a chip with multicore processor architecture.

The communication connection(s) may refer to the hardware/software employed to connect the network interface to the bus. While the communication connection is shown for illustrative clarity inside the computer system 20063, it can also be external to the computer system 20063. The hardware/software necessary for connection to the network interface may include, for illustrative purposes only, internal and external technologies such as modems, including regular telephone-grade modems, cable modems, optical fiber modems, and DSL modems, ISDN adapters, and Ethernet cards. In some examples, the network interface may also be provided using an RF interface.

Surgical data network associated with the surgical hub system 20060 may be configured as passive, intelligent, or switching. A passive surgical data network serves as a conduit for the data, enabling it to go from one device (or segment) to another and to the cloud computing resources. An intelligent surgical data network includes additional features to enable the traffic passing through the surgical data network to be monitored and to configure each port in the network hub 20061 or network switch 20062. An intelligent surgical data network may be referred to as a manageable hub or switch. A switching hub reads the destination address of each packet and then forwards the packet to the correct port.

Modular devices 1a-1n located in the operating theater may be coupled to the modular communication hub 20065. The network hub 20061 and/or the network switch 20062 may be coupled to a network router 20066 to connect the devices 1a-1n to the cloud computing system 20064 or the local computer system 20063. Data associated with the devices 1a-1n may be transferred to cloud-based computers via the router for remote data processing and manipulation. Data associated with the devices 1a-1n may also be transferred to the local computer system 20063 for local data processing and manipulation. Modular devices 2a-2m located in the same operating theater also may be coupled to a network switch 20062. The network switch 20062 may be coupled to the network hub 20061 and/or the network router 20066 to connect the devices 2a-2m to the cloud 20064. Data associated with the devices 2a-2m may be transferred to the cloud computing system 20064 via the network router 20066 for data processing and manipulation. Data associated with the devices 2a-2m may also be transferred to the local computer system 20063 for local data processing and manipulation.

The wearable sensing system 20011 may include one or more sensing systems 20069. The sensing systems 20069 may include an HCP sensing system and/or a patient sensing system. The one or more sensing systems 20069 may be in communication with the computer system 20063 of a surgical hub system 20060 or the cloud server 20067 directly via one of the network routers 20066 or via a network hub 20061 or network switching 20062 that is in communication with the network routers 20066.

The sensing systems 20069 may be coupled to the network router 20066 to connect to the sensing systems 20069 to the local computer system 20063 and/or the cloud computing system 20064. Data associated with the sensing systems 20069 may be transferred to the cloud computing system 20064 via the network router 20066 for data processing and manipulation. Data associated with the sensing systems 20069 may also be transferred to the local computer system 20063 for local data processing and manipulation.

As illustrated in FIG. 4, the surgical hub system 20060 may be expanded by interconnecting multiple network hubs 20061 and/or multiple network switches 20062 with multiple network routers 20066. The modular communication hub 20065 may be contained in a modular control tower configured to receive multiple devices 1a-1n/2a-2m. The local computer system 20063 also may be contained in a modular control tower. The modular communication hub 20065 may be connected to a display 20068 to display images obtained by some of the devices 1a-1n/2a-2m, for example during surgical procedures. In various aspects, the devices 1a-1n/2a-2m may include, for example, various modules such as an imaging module coupled to an endoscope, a generator module coupled to an energy-based surgical device, a smoke evacuation module, a suction/irrigation module, a communication module, a processor module, a storage array, a surgical device coupled to a display, and/or a non-contact sensor module, among other modular devices that may be connected to the modular communication hub 20065 of the surgical data network.

In one aspect, the surgical hub system 20060 illustrated in FIG. 4 may comprise a combination of network hub(s), network switch(es), and network router(s) connecting the devices 1a-1n/2a-2m or the sensing systems 20069 to the cloud-base system 20064. One or more of the devices 1a-1n/2a-2m or the sensing systems 20069 coupled to the network hub 20061 or network switch 20062 may collect data in real-time and transfer the data to cloud computers for data processing and manipulation. It will be appreciated that cloud computing relies on sharing computing resources rather than having local servers or personal devices to handle software applications. The word "cloud" may be used as a metaphor for "the Internet," although the term is not limited as such. Accordingly, the term "cloud computing" may be used herein to refer to "a type of Internet-based computing," where different services—such as servers, storage, and applications—are delivered to the modular communication hub 20065 and/or computer system 20063 located in the surgical theater (e.g., a fixed, mobile, temporary, or field operating room or space) and to devices connected to the modular communication hub 20065 and/or computer system 20063 through the Internet. The cloud infrastructure may be maintained by a cloud service provider. In this context, the cloud service provider may be the entity that coordinates the usage and control of the devices 1a-1n/2a-2m located in one or more operating theaters. The cloud computing services can perform a large number of calculations based on the data gathered by smart surgical instruments, robots, sensing systems, and other computerized devices located in the operating theater. The hub hardware enables multiple devices, sensing systems, and/or connections to be connected to a computer that communicates with the cloud computing resources and storage.

Applying cloud computer data processing techniques on the data collected by the devices 1a-1n/2a-2m, the surgical data network can provide improved surgical outcomes, reduced costs, and improved patient satisfaction. At least some of the devices 1a-1n/2a-2m may be employed to view tissue states to assess leaks or perfusion of sealed tissue after a tissue sealing and cutting procedure. At least some of the devices 1a-1n/2a-2m may be employed to identify pathology, such as the effects of diseases, using the cloud-based computing to examine data including images of samples of body tissue for diagnostic purposes. This may include localization and margin confirmation of tissue and phenotypes. At least some of the devices 1a-1n/2a-2m may be employed to identify anatomical structures of the body using a variety of sensors integrated with imaging devices and techniques such as overlaying images captured by multiple imaging devices. The data gathered by the devices 1a-1n/2a-2m, including image data, may be transferred to the cloud computing system 20064 or the local computer system 20063 or both for data processing and manipulation including image processing and manipulation. The data may be analyzed to improve surgical procedure outcomes by determining if further treatment, such as the application of endoscopic intervention, emerging technologies, a targeted radiation, targeted intervention, and precise robotics to tissue-specific sites and conditions, may be pursued. Such data analysis may further employ outcome analytics processing and using standardized approaches may provide beneficial feedback to either confirm surgical treatments and the behavior of the surgeon or suggest modifications to surgical treatments and the behavior of the surgeon.

Applying cloud computer data processing techniques on the measurement data collected by the sensing systems 20069, the surgical data network can provide improved surgical outcomes, improved recovery outcomes, reduced costs, and improved patient satisfaction. At least some of the sensing systems 20069 may be employed to assess physiological conditions of a surgeon operating on a patient or a patient being prepared for a surgical procedure or a patient recovering after a surgical procedure. The cloud-based computing system 20064 may be used to monitor biomarkers associated with a surgeon or a patient in real-time and to generate surgical plans based at least on measurement data gathered prior to a surgical procedure, provide control signals to the surgical instruments during a surgical procedure, and notify a patient of a complication during post-surgical period.

The operating theater devices 1a-1n may be connected to the modular communication hub 20065 over a wired channel or a wireless channel depending on the configuration of the devices 1a-1n to a network hub 20061. The network hub 20061 may be implemented, in one aspect, as a local network broadcast device that works on the physical layer of the Open System Interconnection (OSI) model. The network hub may provide connectivity to the devices 1a-1n located in the same operating theater network. The network hub 20061 may collect data in the form of packets and sends them to the router in half duplex mode. The network hub 20061 may not store any media access control/Internet Protocol (MAC/IP) to transfer the device data. Only one of the devices 1a-1n can send data at a time through the network hub 20061. The network hub 20061 may not have routing tables or intelligence regarding where to send information and broadcasts all network data across each connection and to a remote server 20067 of the cloud computing system 20064. The network hub 20061 can detect basic network errors such as collisions but having all information broadcast to multiple ports can be a security risk and cause bottlenecks.

The operating theater devices 2a-2m may be connected to a network switch 20062 over a wired channel or a wireless channel. The network switch 20062 works in the data link layer of the OSI model. The network switch 20062 may be a multicast device for connecting the devices 2a-2m located in the same operating theater to the network. The network switch 20062 may send data in the form of frames to the network router 20066 and may work in full duplex mode. Multiple devices 2a-2m can send data at the same time through the network switch 20062. The network switch 20062 stores and uses MAC addresses of the devices 2a-2m to transfer data.

The network hub 20061 and/or the network switch 20062 may be coupled to the network router 20066 for connection to the cloud computing system 20064. The network router 20066 works in the network layer of the OSI model. The network router 20066 creates a route for transmitting data packets received from the network hub 20061 and/or network switch 20062 to cloud-based computer resources for further processing and manipulation of the data collected by any one of or all the devices 1a-1n/2a-2m and wearable sensing system 20011. The network router 20066 may be employed to connect two or more different networks located in different locations, such as, for example, different operating theaters of the same healthcare facility or different networks located in different operating theaters of different healthcare facilities. The network router 20066 may send data in the form of packets to the cloud computing system 20064 and works in full duplex mode. Multiple devices can send data at the same time. The network router 20066 may use IP addresses to transfer data.

In an example, the network hub 20061 may be implemented as a USB hub, which allows multiple USB devices to be connected to a host computer. The USB hub may expand a single USB port into several tiers so that there are more ports available to connect devices to the host system computer. The network hub 20061 may include wired or wireless capabilities to receive information over a wired channel or a wireless channel. In one aspect, a wireless USB short-range, high-bandwidth wireless radio communication protocol may be employed for communication between the devices 1a-1n and devices 2a-2m located in the operating theater.

In examples, the operating theater devices 1a-1n/2a-2m and/or the sensing systems 20069 may communicate to the modular communication hub 20065 via Bluetooth wireless technology standard for exchanging data over short distances (using short-wavelength UHF radio waves in the ISM band from 2.4 to 2.485 GHz) from fixed and mobile devices and building personal area networks (PANs). The operating theater devices 1a-1n/2a-2m and/or the sensing systems 20069 may communicate to the modular communication hub 20065 via a number of wireless or wired communication standards or protocols, including but not limited to Bluetooth, Low-Energy Bluetooth, near-field communication (NFC), Wi-Fi (IEEE 802.11 family), WiMAX (IEEE 802.16 family), IEEE 802.20, new radio (NR), long-term evolution (LTE), and Ev-DO, HSPA+, HSDPA+, HSUPA+, EDGE, GSM, GPRS, CDMA, TDMA, DECT, and Ethernet derivatives thereof, as well as any other wireless and wired protocols that are designated as 3G, 4G, 5G, and beyond. The computing module may include a plurality of communication modules. For instance, a first communication module may be dedicated to shorter-range wireless communications such as Wi-Fi and Bluetooth Low-Energy Bluetooth, Bluetooth Smart, and a second communication module may be dedicated to longer-range wireless communications such as GPS, EDGE, GPRS, CDMA, WiMAX, LTE, Ev-DO, HSPA+, HSDPA+, HSUPA+, EDGE, GSM, GPRS, CDMA, TDMA, and others.

The modular communication hub 20065 may serve as a central connection for one or more of the operating theater devices 1a-1n/2a-2m and/or the sensing systems 20069 and may handle a data type known as frames. Frames may carry the data generated by the devices 1a-1n/2a-2m and/or the sensing systems 20069. When a frame is received by the modular communication hub 20065, it may be amplified and/or sent to the network router 20066, which may transfer the data to the cloud computing system 20064 or the local computer system 20063 by using a number of wireless or wired communication standards or protocols, as described herein.

The modular communication hub 20065 can be used as a standalone device or be connected to compatible network hubs 20061 and network switches 20062 to form a larger network. The modular communication hub 20065 can be generally easy to install, configure, and maintain, making it a good option for networking the operating theater devices 1a-1n/2a-2m.

Figure 5:
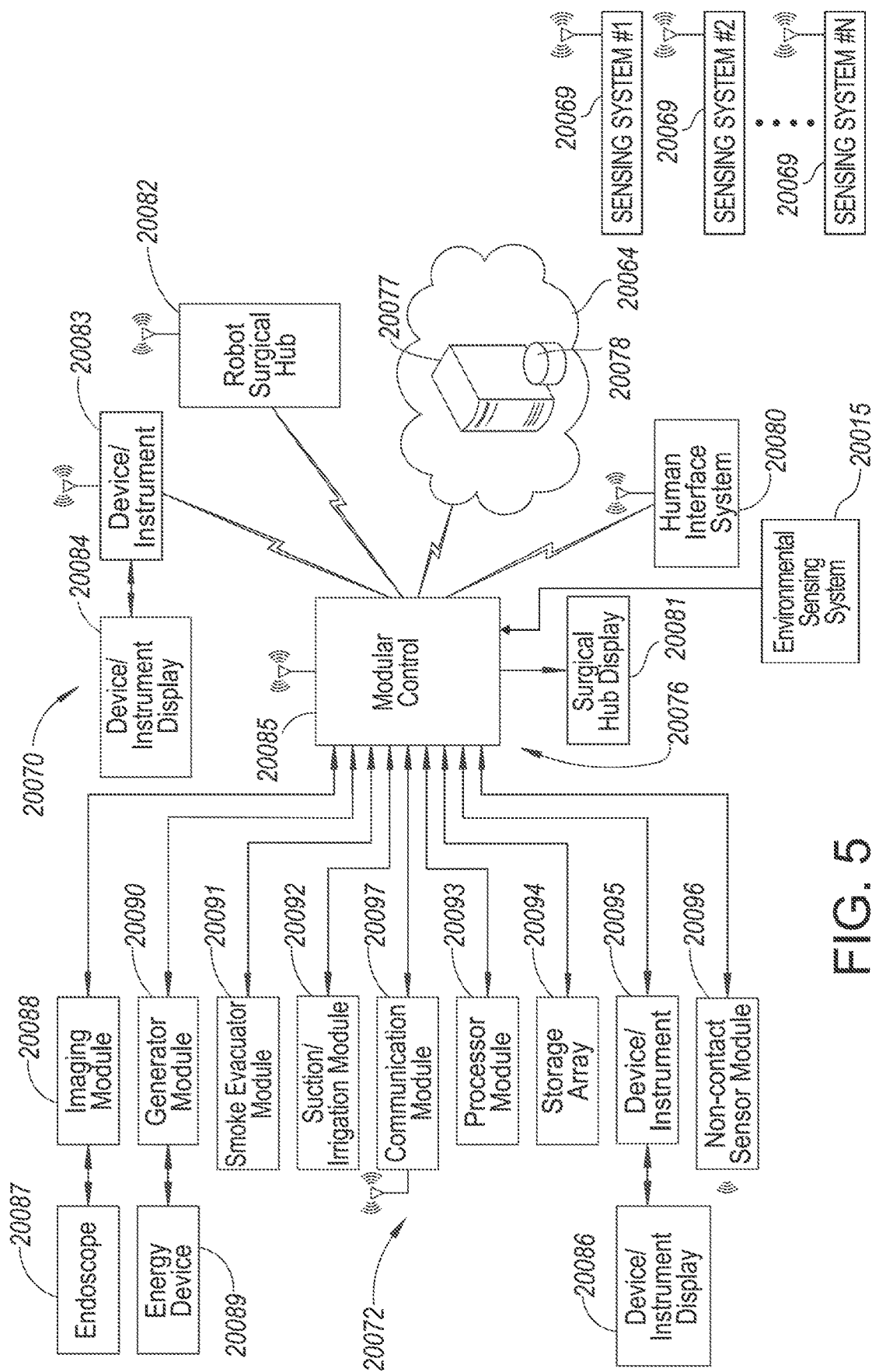
FIG. 5 illustrates an example computer-implemented interactive surgical system that may be part of a surgical system.

FIG. 5 illustrates a computer-implemented interactive surgical system 20070 that may be a part of the Surgical system 20002. The computer-implemented interactive surgical system 20070 is similar in many respects to the HCP sensing system 20002. For example, the computer-implemented interactive surgical system 20070 may include one or more surgical sub-systems 20072, which are similar in many respects to the Surgical systems 20002. Each sub-surgical system 20072 may include at least one surgical hub 20076 in communication with a cloud computing system 20064 that may include a remote server 20077 and a remote storage 20078. In one aspect, the computer-implemented interactive surgical system 20070 may include a modular control 20085 connected to multiple operating theater devices such as sensing systems 20001, intelligent surgical instruments, robots, and other computerized devices located in the operating theater.

As illustrated in the example of FIG. 5, the modular control 20085 may be coupled to an imaging module 20088 that may be coupled to an endoscope 20087, a generator module 20090 that may be coupled to an energy device 20089, a smoke evacuator module 20091, a suction/irrigation module 20092, a communication module 20097, a processor module 20093, a storage array 20094, a smart device/instrument 20095 optionally coupled to a display 20086 and 20084 respectively, and a non-contact sensor module 20096. The non-contact sensor module 20096 may measure the dimensions of the operating theater and generate a map of the surgical theater using, ultrasonic, laser-type, and/or the like, non-contact measurement devices. Other distance sensors can be employed to determine the bounds of an operating room. An ultrasound-based non-contact sensor module may scan the operating theater by transmitting a burst of ultrasound and receiving the echo when it bounces off the perimeter walls of an operating theater as described under the heading "Surgical Hub Spatial Awareness Within an Operating Room" in U.S. Provisional Patent Application Ser. No. 62/611,341, titled INTERACTIVE SURGICAL PLATFORM, filed Dec. 28, 2017, which is herein incorporated by reference in its entirety. The sensor module may be configured to determine the size of the operating theater and to adjust Bluetooth-pairing distance limits. A laser-based non-contact sensor module may scan the operating theater by transmitting laser light pulses, receiving laser light pulses that bounce off the perimeter walls of the operating theater, and comparing the phase of the transmitted pulse to the received pulse to determine the size of the operating theater and to adjust Bluetooth pairing distance limits, for example.

The modular control 20085 may also be in communication with one or more sensing systems 20069 and an environmental sensing system 20015. The sensing systems 20069 may be connected to the modular control 20085 either directly via a router or via the communication module 20097. The operating theater devices may be coupled to cloud computing resources and data storage via the modular control 20085. A robot surgical hub 20082 also may be connected to the modular control 20085 and to the cloud computing resources. The devices/instruments 20095 or 20084, human interface system 20080, among others, may be coupled to the modular control 20085 via wired or wireless communication standards or protocols, as described herein. The human interface system 20080 may include a display sub-system and a notification sub-system. The modular control 20085 may be coupled to a hub display 20081 (e.g., monitor, screen) to display and overlay images received from the imaging module 20088, device/instrument display 20086, and/or other human interface systems 20080. The hub display 20081 also may display data received from devices connected to the modular control 20085 in conjunction with images and overlaid images.

Figure 6:
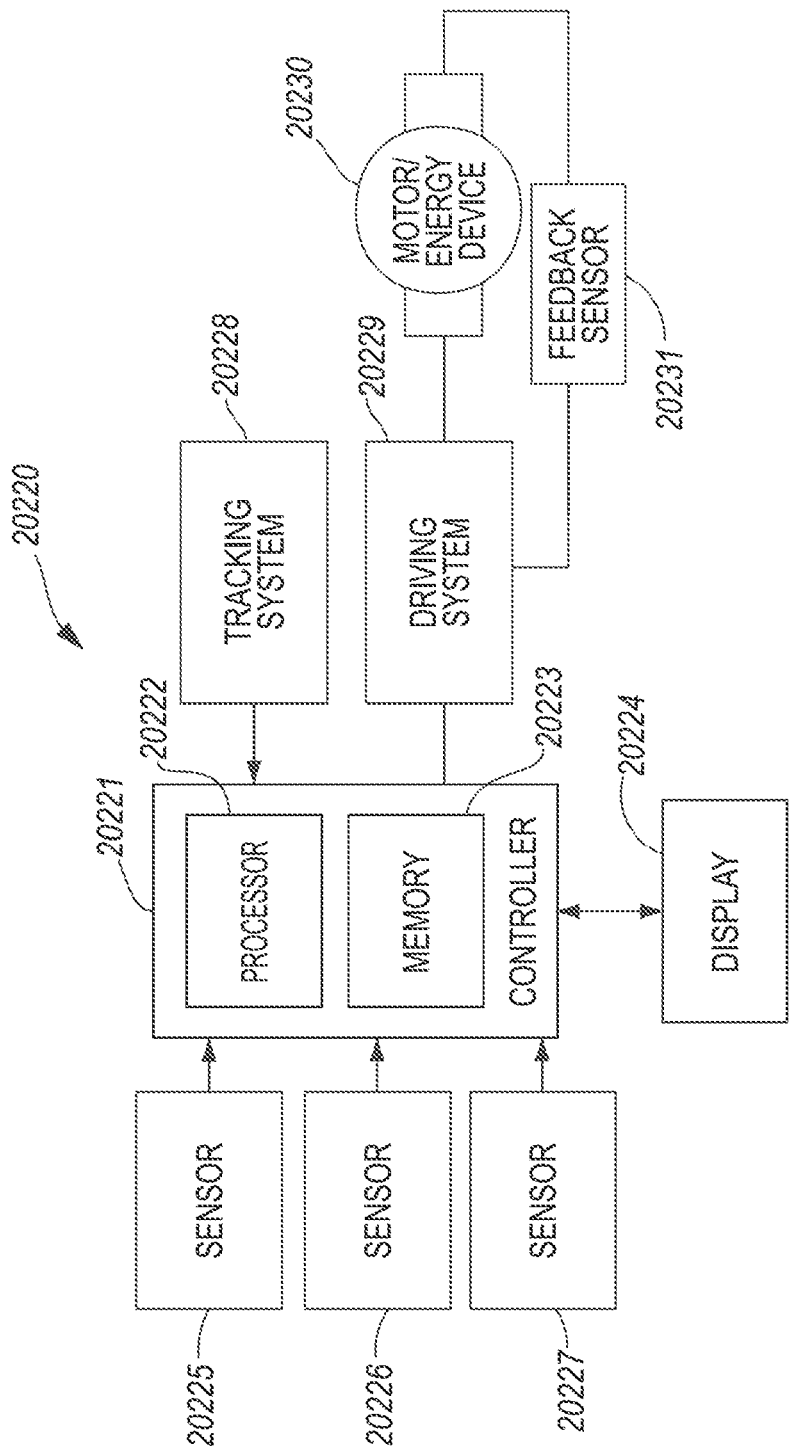
FIG. 6 illustrates a logic diagram of a control system of a surgical instrument.

FIG. 6 illustrates a logical diagram of a control system 20220 of a surgical instrument or a surgical tool in accordance with one or more aspects of the present disclosure. The surgical instrument or the surgical tool may be configurable. The surgical instrument may include surgical fixtures specific to the procedure at-hand, such as imaging devices, surgical staplers, energy devices, endocutter devices, or the like. For example, the surgical instrument may include any of a powered stapler, a powered stapler generator, an energy device, an advanced energy device, an advanced energy jaw device, an endocutter clamp, an energy device generator, an in-operating-room imaging system, a smoke evacuator, a suction-irrigation device, an insufflation system, or the like. The system 20220 may comprise a control circuit. The control circuit may include a microcontroller 20221 comprising a processor 20222 and a memory 20223. One or more of sensors 20225, 20226, 20227, for example, provide real-time feedback to the processor 20222. A motor 20230, driven by a motor driver 20229, operably couples a longitudinally movable displacement member to drive the I-beam knife element. A tracking system 20228 may be configured to determine the position of the longitudinally movable displacement member. The position information may be provided to the processor 20222, which can be programmed or configured to determine the position of the longitudinally movable drive member as well as the position of a firing member, firing bar, and I-beam knife element. Additional motors may be provided at the tool driver interface to control I-beam firing, closure tube travel, shaft rotation, and articulation. A display 20224 may display a variety of operating conditions of the instruments and may include touch screen functionality for data input. Information displayed on the display 20224 may be overlaid with images acquired via endoscopic imaging modules.

The microcontroller 20221 may be any single-core or multicore processor such as those known under the trade name ARM Cortex by Texas Instruments. In one aspect, the main microcontroller 20221 may be an LM4F230H5QR ARM Cortex-M4F Processor Core, available from Texas Instruments, for example, comprising an on-chip memory of 256 KB single-cycle flash memory, or other non-volatile memory, up to 40 MHz, a prefetch buffer to improve performance above 40 MHz, a 32 KB single-cycle SRAM, and internal ROM loaded with StellarisWare® software, a 2 KB EEPROM, one or more PWM modules, one or more QEI analogs, and/or one or more 12-bit ADCs with 12 analog input channels, details of which are available for the product datasheet.

The microcontroller 20221 may comprise a safety controller comprising two controller-based families such as TMS570 and RM4x, known under the trade name Hercules ARM Cortex R4, also by Texas Instruments. The safety controller may be configured specifically for IEC 61508 and ISO 26262 safety critical applications, among others, to provide advanced integrated safety features while delivering scalable performance, connectivity, and memory options.

The microcontroller 20221 may be programmed to perform various functions such as precise control over the speed and position of the knife and articulation systems. In one aspect, the microcontroller 20221 may include a processor 20222 and a memory 20223. The electric motor 20230 may be a brushed direct current (DC) motor with a gearbox and mechanical links to an articulation or knife system. In one aspect, a motor driver 20229 may be an A3941 available from Allegro Microsystems, Inc. Other motor drivers may be readily substituted for use in the tracking system 20228 comprising an absolute positioning system. A detailed description of an absolute positioning system is described in U.S. Patent Application Publication No. 2017/0296213, titled SYSTEMS AND METHODS FOR CONTROLLING A SURGICAL STAPLING AND CUTTING INSTRUMENT, which published on Oct. 19, 2017, which is herein incorporated by reference in its entirety.

The microcontroller 20221 may be programmed to provide precise control over the speed and position of displacement members and articulation systems. The microcontroller 20221 may be configured to compute a response in the software of the microcontroller 20221. The computed response may be compared to a measured response of the actual system to obtain an "observed" response, which is used for actual feedback decisions. The observed response may be a favorable, tuned value that balances the smooth, continuous nature of the simulated response with the measured response, which can detect outside influences on the system.

The motor 20230 may be controlled by the motor driver 20229 and can be employed by the firing system of the surgical instrument or tool. In various forms, the motor 20230 may be a brushed DC driving motor having a maximum rotational speed of approximately 25,000 RPM. In some examples, the motor 20230 may include a brushless motor, a cordless motor, a synchronous motor, a stepper motor, or any other suitable electric motor. The motor driver 20229 may comprise an H-bridge driver comprising field-effect transistors (FETs), for example. The motor 20230 can be powered by a power assembly releasably mounted to the handle assembly or tool housing for supplying control power to the surgical instrument or tool. The power assembly may comprise a battery which may include a number of battery cells connected in series that can be used as the power source to power the surgical instrument or tool. In certain circumstances, the battery cells of the power assembly may be replaceable and/or rechargeable. In at least one example, the battery cells can be lithium-ion batteries which can be couplable to and separable from the power assembly.

The motor driver 20229 may be an A3941 available from Allegro Microsystems, Inc. A3941 may be a full-bridge controller for use with external N-channel power metal-oxide semiconductor field-effect transistors (MOSFETs) specifically designed for inductive loads, such as brush DC motors. The driver 20229 may comprise a unique charge pump regulator that can provide full (>10 V) gate drive for battery voltages down to 7 V and can allow the A3941 to operate with a reduced gate drive, down to 5.5 V. A bootstrap capacitor may be employed to provide the above battery supply voltage required for N-channel MOSFETs. An internal charge pump for the high-side drive may allow DC (100% duty cycle) operation. The full bridge can be driven in fast or slow decay modes using diode or synchronous rectification. In the slow decay mode, current recirculation can be through the high-side or the low-side FETs. The power FETs may be protected from shoot-through by resistor-adjustable dead time. Integrated diagnostics provide indications of undervoltage, overtemperature, and power bridge faults and can be configured to protect the power MOSFETs under most short circuit conditions. Other motor drivers may be readily substituted for use in the tracking system 20228 comprising an absolute positioning system.

The tracking system 20228 may comprise a controlled motor drive circuit arrangement comprising a position sensor 20225 according to one aspect of this disclosure. The position sensor 20225 for an absolute positioning system may provide a unique position signal corresponding to the location of a displacement member. In some examples, the displacement member may represent a longitudinally movable drive member comprising a rack of drive teeth for meshing engagement with a corresponding drive gear of a gear reducer assembly. In some examples, the displacement member may represent the firing member, which could be adapted and configured to include a rack of drive teeth. In some examples, the displacement member may represent a firing bar or the I-beam, each of which can be adapted and configured to include a rack of drive teeth. Accordingly, as used herein, the term displacement member can be used generically to refer to any movable member of the surgical instrument or tool such as the drive member, the firing member, the firing bar, the I-beam, or any element that can be displaced. In one aspect, the longitudinally movable drive member can be coupled to the firing member, the firing bar, and the I-beam. Accordingly, the absolute positioning system can, in effect, track the linear displacement of the I-beam by tracking the linear displacement of the longitudinally movable drive member. In various aspects, the displacement member may be coupled to any position sensor 20225 suitable for measuring linear displacement. Thus, the longitudinally movable drive member, the firing member, the firing bar, or the I-beam, or combinations thereof, may be coupled to any suitable linear displacement sensor. Linear displacement sensors may include contact or non-contact displacement sensors. Linear displacement sensors may comprise linear variable differential transformers (LVDT), differential variable reluctance transducers (DVRT), a slide potentiometer, a magnetic sensing system comprising a movable magnet and a series of linearly arranged Hall effect sensors, a magnetic sensing system comprising a fixed magnet and a series of movable, linearly arranged Hall effect sensors, an optical sensing system comprising a movable light source and a series of linearly arranged photo diodes or photo detectors, an optical sensing system comprising a fixed light source and a series of movable linearly, arranged photodiodes or photodetectors, or any combination thereof.

The electric motor 20230 can include a rotatable shaft that operably interfaces with a gear assembly that is mounted in meshing engagement with a set, or rack, of drive teeth on the displacement member. A sensor element may be operably coupled to a gear assembly such that a single revolution of the position sensor 20225 element corresponds to some linear longitudinal translation of the displacement member. An arrangement of gearing and sensors can be connected to the linear actuator, via a rack and pinion arrangement, or a rotary actuator, via a spur gear or other connection. A power source may supply power to the absolute positioning system and an output indicator may display the output of the absolute positioning system. The displacement member may represent the longitudinally movable drive member comprising a rack of drive teeth formed thereon for meshing engagement with a corresponding drive gear of the gear reducer assembly. The displacement member may represent the longitudinally movable firing member, firing bar, I-beam, or combinations thereof.

A single revolution of the sensor element associated with the position sensor 20225 may be equivalent to a longitudinal linear displacement d1 of the displacement member, where d1 is the longitudinal linear distance that the displacement member moves from point "a" to point "b" after a single revolution of the sensor element coupled to the displacement member. The sensor arrangement may be connected via a gear reduction that results in the position sensor 20225 completing one or more revolutions for the full stroke of the displacement member. The position sensor 20225 may complete multiple revolutions for the full stroke of the displacement member.

A series of switches, where n is an integer greater than one, may be employed alone or in combination with a gear reduction to provide a unique position signal for more than one revolution of the position sensor 20225. The state of the switches may be fed back to the microcontroller 20221 that applies logic to determine a unique position signal corresponding to the longitudinal linear displacement d1+d2+ . . . dn of the displacement member. The output of the position sensor 20225 is provided to the microcontroller 20221. The position sensor 20225 of the sensor arrangement may comprise a magnetic sensor, an analog rotary sensor like a potentiometer, or an array of analog Hall-effect elements, which output a unique combination of position signals or values.

The position sensor 20225 may comprise any number of magnetic sensing elements, such as, for example, magnetic sensors classified according to whether they measure the total magnetic field or the vector components of the magnetic field. The techniques used to produce both types of magnetic sensors may encompass many aspects of physics and electronics. The technologies used for magnetic field sensing may include search coil, fluxgate, optically pumped, nuclear precession, SQUID, Hall-effect, anisotropic magnetoresistance, giant magnetoresistance, magnetic tunnel junctions, giant magnetoimpedance, magnetostrictive/piezoelectric composites, magnetodiode, magnetotransistor, fiber-optic, magneto-optic, and microelectromechanical systems-based magnetic sensors, among others.

The position sensor 20225 for the tracking system 20228 comprising an absolute positioning system may comprise a magnetic rotary absolute positioning system. The position sensor 20225 may be implemented as an AS5055EQFT single-chip magnetic rotary position sensor available from Austria Microsystems, AG. The position sensor 20225 is interfaced with the microcontroller 20221 to provide an absolute positioning system. The position sensor 20225 may be a low-voltage and low-power component and may include four Hall-effect elements in an area of the position sensor 20225 that may be located above a magnet. A high-resolution ADC and a smart power management controller may also be provided on the chip. A coordinate rotation digital computer (CORDIC) processor, also known as the digit-by-digit method and Volder's algorithm, may be provided to implement a simple and efficient algorithm to calculate hyperbolic and trigonometric functions that require only addition, subtraction, bit-shift, and table lookup operations. The angle position, alarm bits, and magnetic field information may be transmitted over a standard serial communication interface, such as a serial peripheral interface (SPI) interface, to the microcontroller 20221. The position sensor 20225 may provide 12 or 14 bits of resolution. The position sensor 20225 may be an AS5055 chip provided in a small QFN 16-pin 4×4×0.85 mm package.

The tracking system 20228 comprising an absolute positioning system may comprise and/or be programmed to implement a feedback controller, such as a PID, state feedback, and adaptive controller. A power source converts the signal from the feedback controller into a physical input to the system: in this case the voltage. Other examples include a PWM of the voltage, current, and force. Other sensor(s) may be provided to measure physical parameters of the physical system in addition to the position measured by the position sensor 20225. In some aspects, the other sensor(s) can include sensor arrangements such as those described in U.S. Pat. No. 9,345,481, titled STAPLE CARTRIDGE TISSUE THICKNESS SENSOR SYSTEM, which issued on May 24, 2016, which is herein incorporated by reference in its entirety; U.S. Patent Application Publication No. 2014/0263552, titled STAPLE CARTRIDGE TISSUE THICKNESS SENSOR SYSTEM, which published on Sep. 18, 2014, which is herein incorporated by reference in its entirety; and U.S. patent application Ser. No. 15/628,175, titled TECHNIQUES FOR ADAPTIVE CONTROL OF MOTOR VELOCITY OF A SURGICAL STAPLING AND CUTTING INSTRUMENT, filed Jun. 20, 2017, which is herein incorporated by reference in its entirety. In a digital signal processing system, an absolute positioning system is coupled to a digital data acquisition system where the output of the absolute positioning system will have a finite resolution and sampling frequency. The absolute positioning system may comprise a compare-and-combine circuit to combine a computed response with a measured response using algorithms, such as a weighted average and a theoretical control loop, that drive the computed response towards the measured response. The computed response of the physical system may take into account properties like mass, inertia, viscous friction, inductance resistance, etc., to predict what the states and outputs of the physical system will be by knowing the input.

The absolute positioning system may provide an absolute position of the displacement member upon power-up of the instrument, without retracting or advancing the displacement member to a reset (zero or home) position as may be required with conventional rotary encoders that merely count the number of steps forwards or backwards that the motor 20230 has taken to infer the position of a device actuator, drive bar, knife, or the like.

A sensor 20226, such as, for example, a strain gauge or a micro-strain gauge, may be configured to measure one or more parameters of the end effector, such as, for example, the amplitude of the strain exerted on the anvil during a clamping operation, which can be indicative of the closure forces applied to the anvil. The measured strain may be converted to a digital signal and provided to the processor 20222. Alternatively, or in addition to the sensor 20226, a sensor 20227, such as, for example, a load sensor, can measure the closure force applied by the closure drive system to the anvil. The sensor 20227, such as, for example, a load sensor, can measure the firing force applied to an I-beam in a firing stroke of the surgical instrument or tool. The I-beam is configured to engage a wedge sled, which is configured to upwardly cam staple drivers to force out staples into deforming contact with an anvil. The I-beam also may include a sharpened cutting edge that can be used to sever tissue as the I-beam is advanced distally by the firing bar. Alternatively, a current sensor 20231 can be employed to measure the current drawn by the motor 20230. The force required to advance the firing member can correspond to the current drawn by the motor 20230, for example. The measured force may be converted to a digital signal and provided to the processor 20222.

For example, the strain gauge sensor 20226 can be used to measure the force applied to the tissue by the end effector. A strain gauge can be coupled to the end effector to measure the force on the tissue being treated by the end effector. A system for measuring forces applied to the tissue grasped by the end effector may comprise a strain gauge sensor 20226, such as, for example, a micro-strain gauge, that can be configured to measure one or more parameters of the end effector, for example. In one aspect, the strain gauge sensor 20226 can measure the amplitude or magnitude of the strain exerted on a jaw member of an end effector during a clamping operation, which can be indicative of the tissue compression. The measured strain can be converted to a digital signal and provided to a processor 20222 of the microcontroller 20221. A load sensor 20227 can measure the force used to operate the knife element, for example, to cut the tissue captured between the anvil and the staple cartridge. A magnetic field sensor can be employed to measure the thickness of the captured tissue. The measurement of the magnetic field sensor also may be converted to a digital signal and provided to the processor 20222.

The measurements of the tissue compression, the tissue thickness, and/or the force required to close the end effector on the tissue, as respectively measured by the sensors 20226, 20227, can be used by the microcontroller 20221 to characterize the selected position of the firing member and/or the corresponding value of the speed of the firing member. In one instance, a memory 20223 may store a technique, an equation, and/or a lookup table which can be employed by the microcontroller 20221 in the assessment.

The control system 20220 of the surgical instrument or tool also may comprise wired or wireless communication circuits to communicate with the modular communication hub 20065 as shown in FIG. 5.

Figure 7:
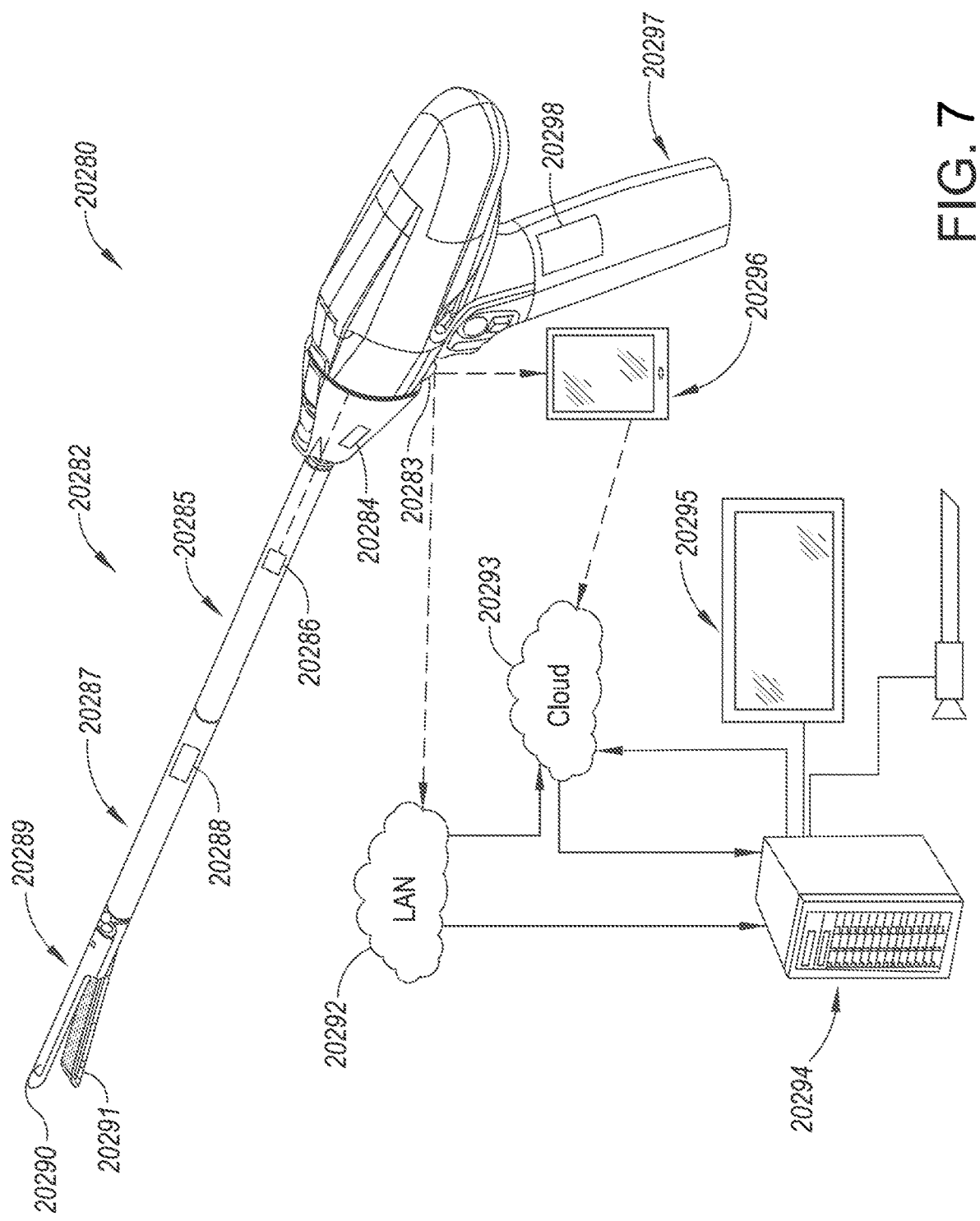
FIG. 7 shows an example surgical system that includes a handle having a controller and a motor, an adapter releasably coupled to the handle, and a loading unit releasably coupled to the adapter.

FIG. 7 illustrates an example surgical system 20280 in accordance with the present disclosure and may include a surgical instrument 20282 that can be in communication with a console 20294 or a portable device 20296 through a local area network 20292 and/or a cloud network 20293 via a wired and/or wireless connection. The console 20294 and the portable device 20296 may be any suitable computing device. The surgical instrument 20282 may include a handle 20297, an adapter 20285, and a loading unit 20287. The adapter 20285 releasably couples to the handle 20297 and the loading unit 20287 releasably couples to the adapter 20285 such that the adapter 20285 transmits a force from a drive shaft to the loading unit 20287. The adapter 20285 or the loading unit 20287 may include a force gauge (not explicitly shown) disposed therein to measure a force exerted on the loading unit 20287. The loading unit 20287 may include an end effector 20289 having a first jaw 20291 and a second jaw 20290. The loading unit 20287 may be an in-situ loaded or multi-firing loading unit (MFLU) that allows a clinician to fire a plurality of fasteners multiple times without requiring the loading unit 20287 to be removed from a surgical site to reload the loading unit 20287.

The first and second jaws 20291, 20290 may be configured to clamp tissue therebetween, fire fasteners through the clamped tissue, and sever the clamped tissue. The first jaw 20291 may be configured to fire at least one fastener a plurality of times or may be configured to include a replaceable multi-fire fastener cartridge including a plurality of fasteners (e.g., staples, clips, etc.) that may be fired more than one time prior to being replaced. The second jaw 20290 may include an anvil that deforms or otherwise secures the fasteners, as the fasteners are ejected from the multi-fire fastener cartridge.

The handle 20297 may include a motor that is coupled to the drive shaft to affect rotation of the drive shaft. The handle 20297 may include a control interface to selectively activate the motor. The control interface may include buttons, switches, levers, sliders, touchscreens, and any other suitable input mechanisms or user interfaces, which can be engaged by a clinician to activate the motor.

The control interface of the handle 20297 may be in communication with a controller 20298 of the handle 20297 to selectively activate the motor to affect rotation of the drive shafts. The controller 20298 may be disposed within the handle 20297 and may be configured to receive input from the control interface and adapter data from the adapter 20285 or loading unit data from the loading unit 20287. The controller 20298 may analyze the input from the control interface and the data received from the adapter 20285 and/or loading unit 20287 to selectively activate the motor. The handle 20297 may also include a display that is viewable by a clinician during use of the handle 20297. The display may be configured to display portions of the adapter or loading unit data before, during, or after firing of the instrument 20282.

The adapter 20285 may include an adapter identification device 20284 disposed therein and the loading unit 20287 may include a loading unit identification device 20288 disposed therein. The adapter identification device 20284 may be in communication with the controller 20298, and the loading unit identification device 20288 may be in communication with the controller 20298. It will be appreciated that the loading unit identification device 20288 may be in communication with the adapter identification device 20284, which relays or passes communication from the loading unit identification device 20288 to the controller 20298.

The adapter 20285 may also include a plurality of sensors 20286 (one shown) disposed thereabout to detect various conditions of the adapter 20285 or of the environment (e.g., if the adapter 20285 is connected to a loading unit, if the adapter 20285 is connected to a handle, if the drive shafts are rotating, the torque of the drive shafts, the strain of the drive shafts, the temperature within the adapter 20285, a number of firings of the adapter 20285, a peak force of the adapter 20285 during firing, a total amount of force applied to the adapter 20285, a peak retraction force of the adapter 20285, a number of pauses of the adapter 20285 during firing, etc.). The plurality of sensors 20286 may provide an input to the adapter identification device 20284 in the form of data signals. The data signals of the plurality of sensors 20286 may be stored within or be used to update the adapter data stored within the adapter identification device 20284. The data signals of the plurality of sensors 20286 may be analog or digital. The plurality of sensors 20286 may include a force gauge to measure a force exerted on the loading unit 20287 during firing.

The handle 20297 and the adapter 20285 can be configured to interconnect the adapter identification device 20284 and the loading unit identification device 20288 with the controller 20298 via an electrical interface. The electrical interface may be a direct electrical interface (i.e., include electrical contacts that engage one another to transmit energy and signals therebetween). Additionally, or alternatively, the electrical interface may be a non-contact electrical interface to wirelessly transmit energy and signals therebetween (e.g., inductively transfer). It is also contemplated that the adapter identification device 20284 and the controller 20298 may be in wireless communication with one another via a wireless connection separate from the electrical interface.

The handle 20297 may include a transceiver 20283 that is configured to transmit instrument data from the controller 20298 to other components of the system 20280 (e.g., the LAN 20292, the cloud 20293, the console 20294, or the portable device 20296). The controller 20298 may also transmit instrument data and/or measurement data associated with one or more sensors 20286 to a surgical hub. The transceiver 20283 may receive data (e.g., cartridge data, loading unit data, adapter data, or other notifications) from the surgical hub 20270. The transceiver 20283 may receive data (e.g., cartridge data, loading unit data, or adapter data) from the other components of the system 20280. For example, the controller 20298 may transmit instrument data including a serial number of an attached adapter (e.g., adapter 20285) attached to the handle 20297, a serial number of a loading unit (e.g., loading unit 20287) attached to the adapter 20285, and a serial number of a multi-fire fastener cartridge loaded into the loading unit to the console 20294. Thereafter, the console 20294 may transmit data (e.g., cartridge data, loading unit data, or adapter data) associated with the attached cartridge, loading unit, and adapter, respectively, back to the controller 20298. The controller 20298 can display messages on the local instrument display or transmit the message, via transceiver 20283, to the console 20294 or the portable device 20296 to display the message on the display 20295 or portable device screen, respectively.

Figure 8:
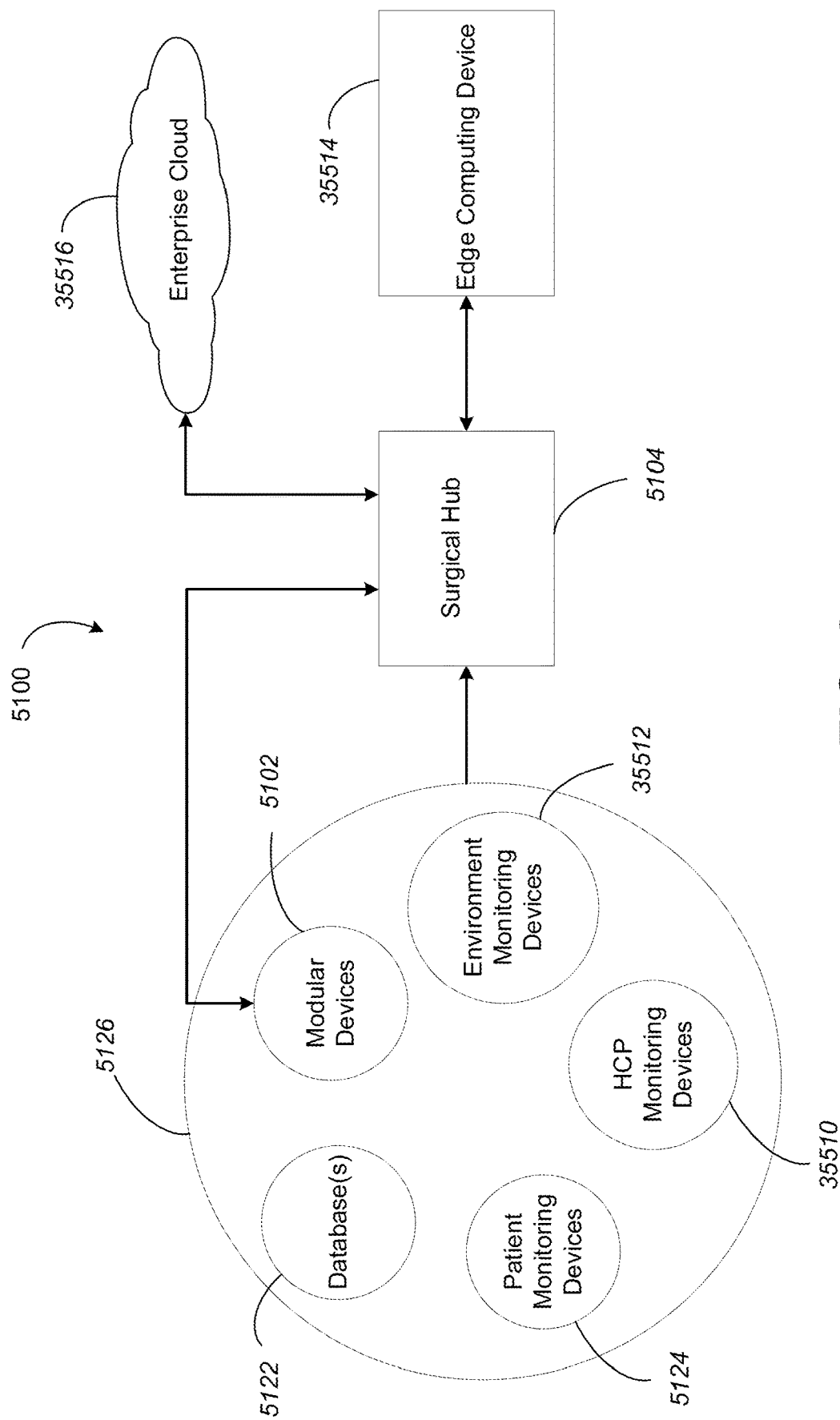
FIG. 8 shows an example situationally aware surgical system.

FIG. 8 illustrates a diagram of a situationally aware surgical system 5100, in accordance with at least one aspect of the present disclosure. The data sources 5126 may include, for example, the modular devices 5102 (which can include sensors configured to detect parameters associated with the patient, HCPs and environment and/or the modular device itself), databases 5122 (e.g., an EMR database containing patient records), patient monitoring devices 5124 (e.g., a blood pressure (BP) monitor and an electrocardiography (EKG) monitor), HCP monitoring devices 35510, and/or environment monitoring devices 35512. The surgical hub 5104 can be configured to derive the contextual information pertaining to the surgical procedure from the data based upon, for example, the particular combination(s) of received data or the particular order in which the data is received from the data sources 5126. The contextual information inferred from the received data can include, for example, the type of surgical procedure being performed, the particular step of the surgical procedure that the surgeon is performing, the type of tissue being operated on, or the body cavity that is the subject of the procedure. This ability by some aspects of the surgical hub 5104 to derive or infer information related to the surgical procedure from received data can be referred to as "situational awareness." For example, the surgical hub 5104 can incorporate a situational awareness system, which is the hardware and/or programming associated with the surgical hub 5104 that derives contextual information pertaining to the surgical procedure from the received data and/or a surgical plan information received from the edge computing system 35514 or an enterprise cloud server 35516.

The situational awareness system of the surgical hub 5104 can be configured to derive the contextual information from the data received from the data sources 5126 in a variety of different ways. For example, the situational awareness system can include a pattern recognition system, or machine learning system (e.g., an artificial neural network), that has been trained on training data to correlate various inputs (e.g., data from database(s) 5122, patient monitoring devices 5124, modular devices 5102, HCP monitoring devices 35510, and/or environment monitoring devices 35512) to corresponding contextual information regarding a surgical procedure. A machine learning system can be trained to accurately derive contextual information regarding a surgical procedure from the provided inputs. In examples, the situational awareness system can include a lookup table storing pre-characterized contextual information regarding a surgical procedure in association with one or more inputs (or ranges of inputs) corresponding to the contextual information. In response to a query with one or more inputs, the lookup table can return the corresponding contextual information for the situational awareness system for controlling the modular devices 5102. In examples, the contextual information received by the situational awareness system of the surgical hub 5104 can be associated with a particular control adjustment or set of control adjustments for one or more modular devices 5102. In examples, the situational awareness system can include a further machine learning system, lookup table, or other such system, which generates or retrieves one or more control adjustments for one or more modular devices 5102 when provided the contextual information as input.

A surgical hub 5104 incorporating a situational awareness system can provide a number of benefits for the surgical system 5100. One benefit may include improving the interpretation of sensed and collected data, which would in turn improve the processing accuracy and/or the usage of the data during the course of a surgical procedure. To return to a previous example, a situationally aware surgical hub 5104 could determine what type of tissue was being operated on; therefore, when an unexpectedly high force to close the surgical instrument's end effector is detected, the situationally aware surgical hub 5104 could correctly ramp up or ramp down the motor of the surgical instrument for the type of tissue.

The type of tissue being operated can affect the adjustments that are made to the compression rate and load thresholds of a surgical stapling and cutting instrument for a particular tissue gap measurement. A situationally aware surgical hub 5104 could infer whether a surgical procedure being performed is a thoracic or an abdominal procedure, allowing the surgical hub 5104 to determine whether the tissue clamped by an end effector of the surgical stapling and cutting instrument is lung (for a thoracic procedure) or stomach (for an abdominal procedure) tissue. The surgical hub 5104 could then adjust the compression rate and load thresholds of the surgical stapling and cutting instrument appropriately for the type of tissue.

The type of body cavity being operated in during an insufflation procedure can affect the function of a smoke evacuator. A situationally aware surgical hub 5104 could determine whether the surgical site is under pressure (by determining that the surgical procedure is utilizing insufflation) and determine the procedure type. As a procedure type can be generally performed in a specific body cavity, the surgical hub 5104 could then control the motor rate of the smoke evacuator appropriately for the body cavity being operated in. Thus, a situationally aware surgical hub 5104 could provide a consistent amount of smoke evacuation for both thoracic and abdominal procedures.

The type of procedure being performed can affect the optimal energy level for an ultrasonic surgical instrument or radio frequency (RF) electrosurgical instrument to operate at. Arthroscopic procedures, for example, may require higher energy levels because the end effector of the ultrasonic surgical instrument or RF electrosurgical instrument is immersed in fluid. A situationally aware surgical hub 5104 could determine whether the surgical procedure is an arthroscopic procedure. The surgical hub 5104 could then adjust the RF power level or the ultrasonic amplitude of the generator (e.g., "energy level") to compensate for the fluid filled environment. Relatedly, the type of tissue being operated on can affect the optimal energy level for an ultrasonic surgical instrument or RF electrosurgical instrument to operate at. A situationally aware surgical hub 5104 could determine what type of surgical procedure is being performed and then customize the energy level for the ultrasonic surgical instrument or RF electrosurgical instrument, respectively, according to the expected tissue profile for the surgical procedure. Furthermore, a situationally aware surgical hub 5104 can be configured to adjust the energy level for the ultrasonic surgical instrument or RF electrosurgical instrument throughout the course of a surgical procedure, rather than just on a procedure-by-procedure basis. A situationally aware surgical hub 5104 could determine what step of the surgical procedure is being performed or will subsequently be performed and then update the control algorithms for the generator and/or ultrasonic surgical instrument or RF electrosurgical instrument to set the energy level at a value appropriate for the expected tissue type according to the surgical procedure step.

In examples, data can be drawn from additional data sources 5126 to improve the conclusions that the surgical hub 5104 draws from one data source 5126. A situationally aware surgical hub 5104 could augment data that it receives from the modular devices 5102 with contextual information that it has built up regarding the surgical procedure from other data sources 5126. For example, a situationally aware surgical hub 5104 can be configured to determine whether hemostasis has occurred (e.g., whether bleeding at a surgical site has stopped) according to video or image data received from a medical imaging device. The surgical hub 5104 can be further configured to compare a physiologic measurement (e.g., blood pressure sensed by a BP monitor communicably connected to the surgical hub 5104) with the visual or image data of hemostasis (e.g., from a medical imaging device communicably coupled to the surgical hub 5104) to make a determination on the integrity of the staple line or tissue weld. The situational awareness system of the surgical hub 5104 can consider the physiological measurement data to provide additional context in analyzing the visualization data. The additional context can be useful when the visualization data may be inconclusive or incomplete on its own.

For example, a situationally aware surgical hub 5104 could proactively activate the generator to which an RF electrosurgical instrument is connected if it determines that a subsequent step of the procedure requires the use of the instrument. Proactively activating the energy source can allow the instrument to be ready for use as soon as the preceding step of the procedure is completed.

The situationally aware surgical hub 5104 could determine whether the current or subsequent step of the surgical procedure requires a different view or degree of magnification on the display according to the feature(s) at the surgical site that the surgeon is expected to need to view. The surgical hub 5104 could proactively change the displayed view (supplied by, e.g., a medical imaging device for the visualization system) accordingly so that the display automatically adjusts throughout the surgical procedure.

The situationally aware surgical hub 5104 could determine which step of the surgical procedure is being performed or will subsequently be performed and whether particular data or comparisons between data will be required for that step of the surgical procedure. The surgical hub 5104 can be configured to automatically call up data screens based upon the step of the surgical procedure being performed, without waiting for the surgeon to ask for the particular information.

Errors may be checked during the setup of the surgical procedure or during the course of the surgical procedure. For example, the situationally aware surgical hub 5104 could determine whether the operating theater is setup properly or optimally for the surgical procedure to be performed. The surgical hub 5104 can be configured to determine the type of surgical procedure being performed, retrieve the corresponding checklists, product location, or setup needs (e.g., from a memory), and then compare the current operating theater layout to the standard layout for the type of surgical procedure that the surgical hub 5104 determines is being performed. In some exemplifications, the surgical hub 5104 can compare the list of items for the procedure and/or a list of devices paired with the surgical hub 5104 to a recommended or anticipated manifest of items and/or devices for the given surgical procedure. If there are any discontinuities between the lists, the surgical hub 5104 can provide an alert indicating that a particular modular device 5102, patient monitoring device 5124, HCP monitoring device 35510, environment monitoring devices 35512, and/or other surgical item is missing. In some examples, the surgical hub 5104 can determine the relative distance or position of the modular devices 5102 and patient monitoring devices 5124 via proximity sensors, for example. The surgical hub 5104 can compare the relative positions of the devices to a recommended or anticipated layout for the particular surgical procedure. If there are any discontinuities between the layouts, the surgical hub 5104 can be configured to provide an alert indicating that the current layout for the surgical procedure deviates from the recommended layout.

The situationally aware surgical hub 5104 could determine whether the surgeon (or other HCP(s)) was making an error or otherwise deviating from the expected course of action during the course of a surgical procedure. For example, the surgical hub 5104 can be configured to determine the type of surgical procedure being performed, retrieve the corresponding list of steps or order of equipment usage (e.g., from a memory), and then compare the steps being performed or the equipment being used during the course of the surgical procedure to the expected steps or equipment for the type of surgical procedure that the surgical hub 5104 determined is being performed. The surgical hub 5104 can provide an alert indicating that an unexpected action is being performed or an unexpected device is being utilized at the particular step in the surgical procedure.

The surgical instruments (and other modular devices 5102) may be adjusted for the particular context of each surgical procedure (such as adjusting to different tissue types) and validating actions during a surgical procedure. Next steps, data, and display adjustments may be provided to surgical instruments (and other modular devices 5102) in the surgical theater according to the specific context of the procedure.

Systems and/or instrumentalities may be provided for a surgical hub of a surgical system to pair and/or control one or more modules and/or devices located within an operating room. As described in FIG. 3 or FIG. 5, a surgical system may include a surgical hub that is communicatively connected to a plurality of modules, for example, a generator module, a smoke evacuation module, etc. The surgical hub may include a control circuit that may enable the surgical hub for form and/or remove pairings with and/or among devices of the surgical system. The surgical hub may enable the communication module to selectively pair one or more surgical devices that may be used in a surgical procedure.

In an example that involves the situational awareness, the surgical hub may selectively connect or disconnect devices of the surgical system within an operating room based on the type of surgical procedure being performed or based on a determination of an upcoming step of the surgical procedure that requires the devices to be connected or disconnected. The hub situational awareness is described in greater detail below in connection with FIG. 8.

Referring to FIG. 8, the surgical hub may track the progression of surgical steps in a surgical procedure and may coordinate pairing and unpairing of the devices of the surgical system based upon such progression. For example, the surgical hub may determine that a first surgical step requires use of a first surgical instrument, while a second surgical step, occurring after completion of the first surgical step, requires use of a second surgical instrument. Accordingly, the surgical hub may assign a surgical instrument controller to the first surgical instrument for the duration of the first surgical step. After detecting completion of the first surgical step, the surgical hub may cause the communication link between the first surgical instrument and the surgical instrument controller to be severed. The surgical hub may then assign the surgical instrument controller to the second surgical instrument by pairing or authorizing the establishment of a communication link between the surgical instrument controller and the second surgical instrument.

A surgical system may include one or more interconnected surgical hubs that may be connected to one or more edge computing devices and an enterprise cloud system, as described herein in FIG. 1C. The surgical hubs and the computing edge devices may be located within a HIPPA boundary. Each of the surgical hubs may be associated with one or more system modules and/or modular devices (as described in connection with FIG. 3, for example). The system modules may be receivable within a surgical hub and the modular devices or surgical devices or instruments may be connected to the various system modules to connect or pair with the corresponding surgical hub. The connection or paring may be through wired or wireless medium. The modular devices may include intelligent surgical instruments, medical imaging devices, suction/irrigation modules, smoke evacuator module, energy generators, ventilators, insufflators, and surgical hub displays. The modular devices described herein may be controlled by control algorithms or control programs. The control algorithms or control programs may be executed on one or more modular devices, or on one or more surgical hubs to which the modular devices are paired, or on both the modular devices and the surgical hubs, for example, using a distributed computing architecture, as described herein. In an example, control programs associated with the modular devices may control the modular devices based on data sensed by the modular device itself (e.g., by sensors in, on, or connected to the modular device). This data may be related to the patient being operated on (e.g., insufflation pressure) or the modular device itself (e.g., the rate at which a smoke evacuation module is removing gas and particles from the abdomen of a patient).

A plurality of operating rooms located in multiple locations may each be equipped with a surgical hub. The surgical hubs may be connected to one or more edge computing devices. The edge computing devices may be used as an extension of processing and/or storage capabilities of each of the surgical hubs. One of the surgical hubs or the edge computing device may act as a controller that may control interactions between the surgical hubs, the system modules and/or the modular devices associated with each of the surgical hubs. The control interactions between the system modules and/or the modular devices associated with one or more surgical hubs may be based on one of the control schemes including, for example, a cooperative control scheme, a notification control scheme, an antagonistic control scheme, or a hierarchical control scheme. A surgical hub may switch (e.g., adaptively switch) control scheme(s) associated with one or more system modules or one or more modular devices from a first control scheme to a second control scheme.

One or more surgical hubs as well as system modules and/or modular devices associated with the surgical hubs may use cooperative control scheme. In case of a cooperative control scheme, a system module or a modular device may have a functional operation that is part of a linked surgical system. Each of the system modules and/or modular devices that are part of a surgical system may be in communication with the other system modules and/or modular devices. The system modules and/or modular devices may exchange information with the other system modules and/or modular devices thereby having the ability to impact operations of the system modules and/or modular devices associated with the surgical system.

In an example, each of an insufflator system module providing insufflation services and a smoke evacuator system module, as described herein, may have separate and/or independent metering of gas functions. For example, the smoke evacuation system module may be used for removing gas and particles from a patient's abdomen based on the activation and visibility concerns from an energy device. The insufflation system module may be used for pumping $CO_2$ to keep the patient's abdomen inflated, for example, at a predefined pressure. The smoke evacuation system module may be in communication with the insufflation system module. The smoke evacuation system module and the insufflation system module may communicate via a surgical hub or directly over one of the communication interfaces using a peer-to-peer control link (e.g., as described in FIG. 1C and FIG. 10). The smoke evacuation system module and the insufflation system module may set their capacity ranges such that operation of one system does not overwhelm that of the other. In an example, one of the smoke evacuation system modules or one of the insufflation system modules may determine that it may exceed other system module's capacity. For example, the insufflation system module may determine that the highest rate at which it may be able to pump $CO_2$ into the patient's abdomen is less than the rate at which the smoke evacuation system module may remove the $CO_2$ gas and other particles. In such a case, the insufflation system may indicate (e.g., indicate first) to the smoke evacuation system module to reduce its evacuation response in order to better balance the two system modules. The insufflation system may send control messages or control programs (e.g., via the surgical hub or directly) to the smoke evacuation system module indicating to the smoke evacuation system module to reduce its evacuation rate.

One or more surgical hubs as well as system modules or modular devices associated with the surgical hubs may use notification control scheme, for example, to notify (e.g., via a notification message or a control program) a first system module or a modular device about its function to a second system module or a modular device. The first system module or the modular device may send notification messages or control programs to the second system module or modular device without the second system module or modular device being able to change the first system module's or modular device's operation. In an example, the first system module or the modular device may send notification messages or control programs to the second system module or modular device via one of the surgical hubs that may be a part of a surgical system. In an example, the first system module or the modular device may send notification messages or control programs to the second system module or modular device directly, for example, using peer-to-peer control messages.

In an example, a surgical system among other system modules and/or modular devices may include a monopolar generator. A user may request activation of the monopolar generator. A surgical hub that is part of the surgical system may use sensing mechanisms and/or visual mechanisms to initiate activation and pairing of the monopolar generator. The surgical hub may perform the sensing and/or pairing operations based on situational awareness information indicating the use of the monopolar generator in an upcoming step of a surgical procedure. The monopolar generator may send one or more notification messages to other advanced energy modular devices and/or system modules. The notification messages may indicate to the other advanced energy modular devices and/or system modules about the activation and/or the power level of the monopolar generator, for example, to warn the other advanced energy modular devices and/or system modules of the anticipated disruption in their sensing systems while active. The notification messages may also indicate a time interval during which the monopolar generator may be active. The notification messages may act as a warning to the other advanced energy modular devices and/or system modules and enable them to ignore a predefined noise interference that may be caused by the operation of the monopolar generator. The notification messages may also enable the other advanced energy modular devices and/or system modules to not interpret the noise caused by the operation of the monopolar generator as unintended noise and/or unexpected changes, for example, in a system module's monitoring functionality. While the notification messages from the monopolar generator to the other advanced energy modular devices and/or system modules may inform them about the monopolar generator's activation/operation, none of the other advanced energy modular devices and/or system modules in case of notification control scheme may be able to indicate to the monopolar generator to deactivate or activate.

One or more surgical hubs as well as system modules or modular devices associated with the surgical hubs may use an antagonistic control scheme. An antagonistic control scheme may allow a plurality of system modules and/or modular devices contesting for the same system resources to offset each other, thereby changing the balance of the system resources from one system module or modular device to another system module or modular device. In an example, under antagonistic control scheme, the balance of the system resources may be changed based on the priority associated with the task or the priority of the system involved.

In an example, one or more system modules and/or modular devices associated with a surgical system may need additional power, communication, or processing resources while the resources being used by the system modules and/or the modular devices of the surgical system are also being shared with another system module or modular device. For example, a storage module may attempt to upload data to an edge computing device or download data from a cloud service, and an advanced visualization system may also need resources (e.g., computing resources) or the power being used by the storage module to process and/or display the visualization information. In such a case, based on, for example, priority of system module, the system module or the modular device with higher priority may pull the resources that it may share with another system module or the modular device with lower priority. For example, the advanced visualization system over the storage module, the advanced visualization system may pull the resources that it may share with the storage module. Once no longer being utilized by the advanced visualization system, it may return the resources back to the other processes, modules, or devices. The pulling and pushing of resources may imply that there may be a tradeoff between these systems since there is not infinite resources to be shared.

The prioritization of one process, system module, or modular device over other process, system module, or modular device may be based on the importance of the module or function to the task at hand. For example, one or more modules may have inherent higher priority, while performing tasks including, for example, critical (e.g., life critical) tasks, insufflation, etc. In an example, a process, system module, or modular device may have higher priority over another process, system module, or modular device based on external monitored aspects, including for example, surgeon selection, network bandwidth, network down time, or priority value associated with the data, etc.

One or more surgical hubs as well as system modules or modular devices associated with the surgical hubs may use hierarchical control scheme. A hierarchical control scheme may include a hierarchy of control. In an example, a surgical hub may be the main control and decision making element of a surgical system. In another example, the hierarchical control scheme may define a hierarchy (e.g., predefined hierarchy) of system modules, and/or modular devices. In such a case, a system module, or modular device may be configured as the main control and/or decision making element for a set of system modules, or modular devices.

The hierarchical control scheme may be based on a tree with the surgical hub or one of the system modules, or a modular device being a master, and one or more system modules and/or modular device being the subordinate modules and/or modular devices. Control information or control program generated at the surgical hub or the system module acting as a master may be sent to the subordinate system modules and/or modular devices.

In an example, the control interactions between the surgical hub and system modules/modular devices or among the system modules or modular devices on may be based on the type of the system modules/modular devices involved and/or priorities of the processes within the surgical hub that are associated with the system modules and/or modular devices.

Figure 9:
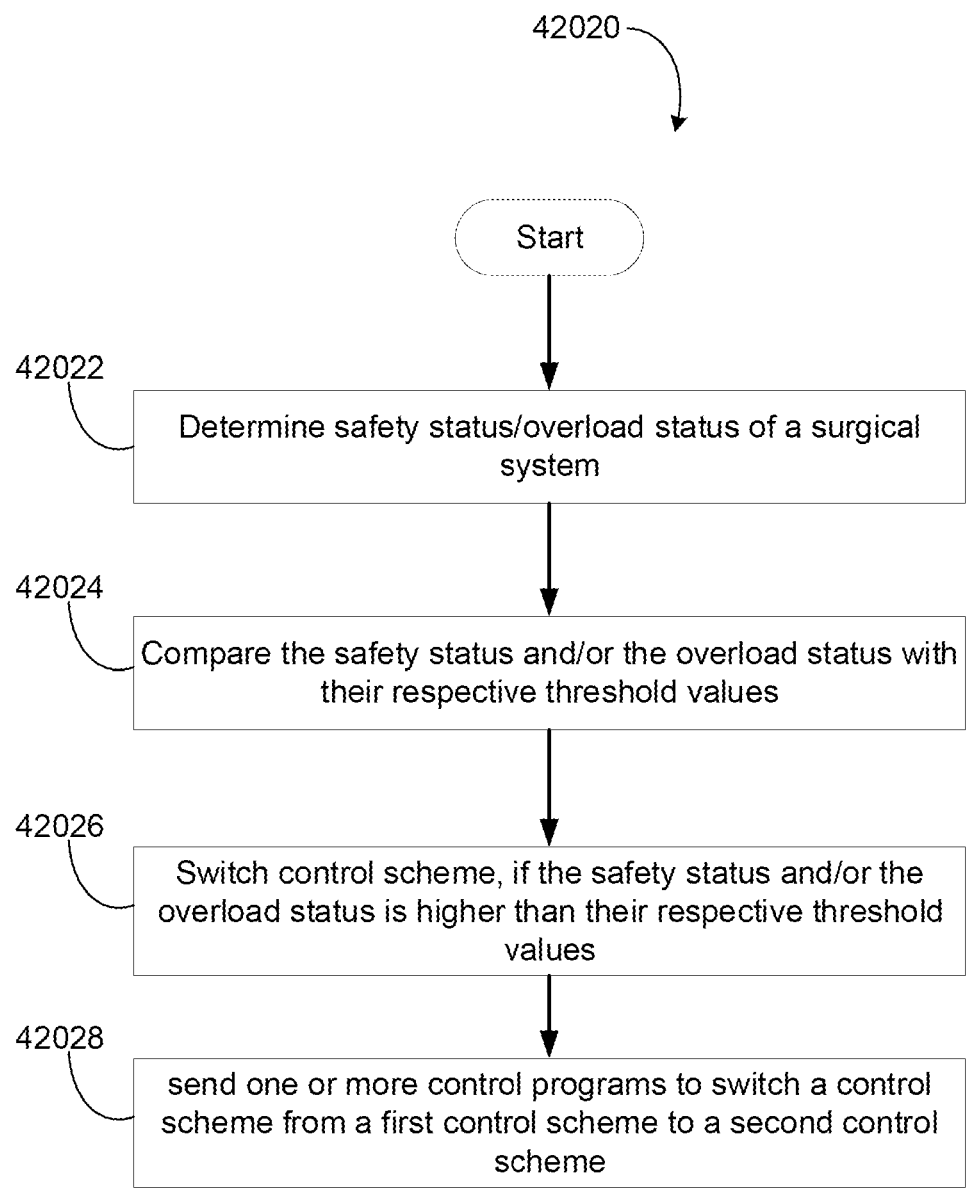
FIG. 9 is a flow diagram illustrating switching of control scheme.

FIG. 9 illustrates an example 42020 of a surgical hub switching a control scheme from a first control scheme to a second control scheme. At 42022, a surgical hub or a master system module or a master modular device may determine safety status and/or overload status of a surgical system. At 42024, the surgical hub or the master system module or the master modular device may compare the safety status and/or the overload status with their respective threshold values (e.g., a predetermined threshold values). At 42026, the surgical hub or the master system module or the master modular device may make a determination of switching the control scheme associated with the surgical hub and/or the modular devices, for example, if the safety status and/or the overload status of the surgical system risk is higher than the respective threshold values. At 42028, the surgical hub or the master system module or the master modular device may send one or more control programs to switch a control scheme from a first control scheme (e.g., a notification control scheme) to a second control scheme (e.g., a hierarchical or an antagonistic control scheme). The switching of the control schemes may be performed, for example, to prevent the system from exceeding maximum limits of the system (e.g., maximum limits of the surgical hub).

Examples described herein may relate to the interconnection of system modules and/or modular devices. The interconnection may include one or more of the following connection types: individual, redundant, smart, or dumb.

Figure 10:
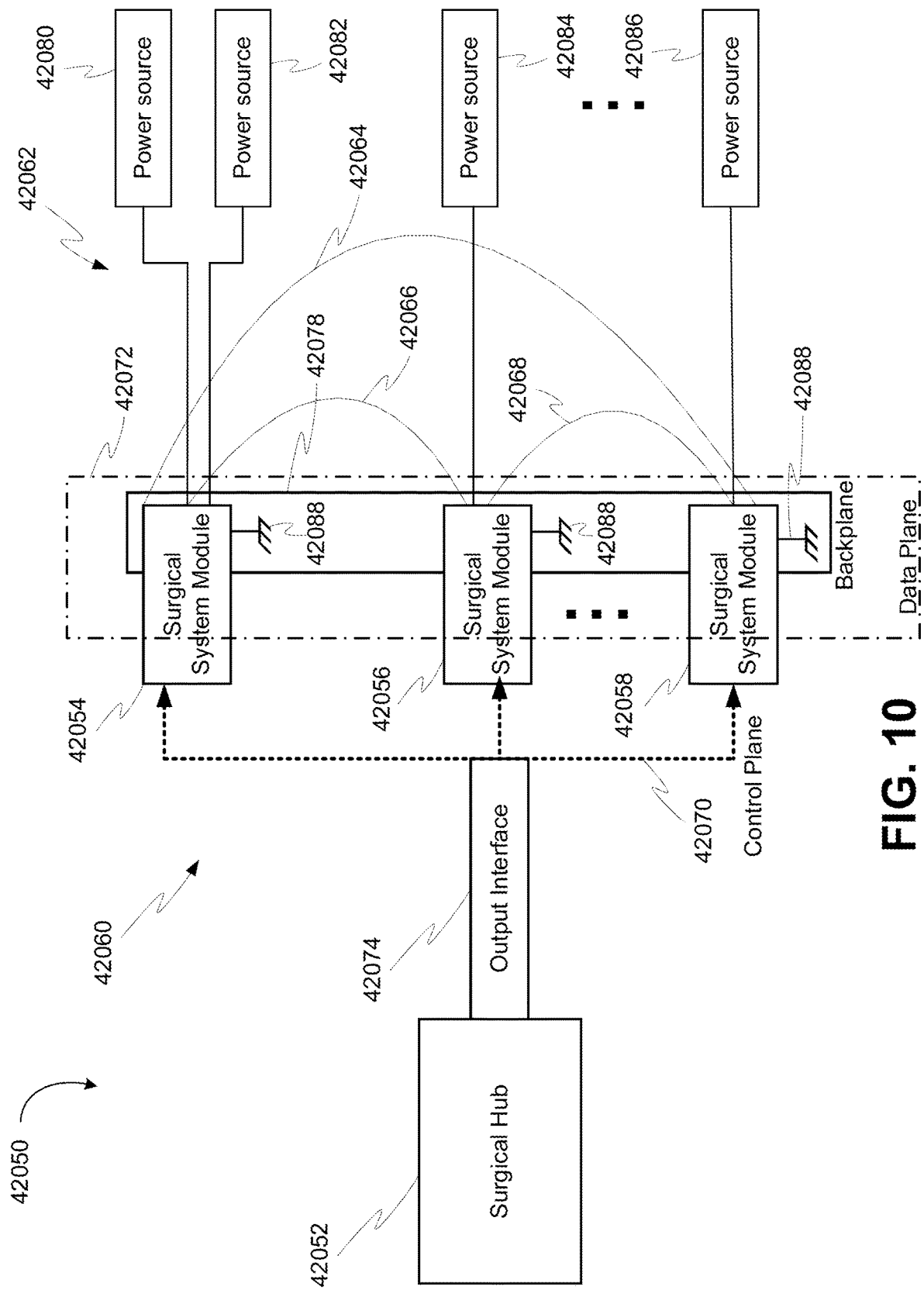
FIG. 10 illustrates an example of a surgical system with physical and communication connections among the surgical system modules, and between the surgical system modules and a surgical hub.

FIG. 10 shows an example of a surgical system 42050 with physical and communication connections between surgical system modules and a surgical hub. The surgical system 42050 may include one or more surgical hubs (e.g., a surgical hub 42052) and one or more surgical system modules (e.g., surgical system modules 42054, 42056, 42058). The surgical hub 42052 may have the capacity for the surgical system modules 42054, 42056, 42058 to be cumulatively coupled via a first port 42060 as well as directly coupled via a second port 42062 simultaneously. The interconnectivity of the surgical system modules 42054, 42056, 42058 may enable some of the surgical system modules 42054, 42056, 42058 to work cooperatively with the exclusion of some of the other surgical system modules 42054, 42056, 42058 or receive data and control from multiple surgical system modules 42054, 42056, 42058 simultaneously. The first port 42060 may include a control plane 42070, a data plane 42072, and a backplane 42078 that facilitate data communication between each of the surgical system modules 42054, 42056, 42058 and the surgical hub 42052. The second port 42062 may be external wired connections 42064, 42066, 42068 connecting each of the surgical system modules 42054, 42056, 42058 to each other separate from the first port 42060. The surgical hub 42052 may include an output interface 42074 that may interface with each of the surgical system modules 42054, 42056, 42058. The connections between the surgical system modules 42054, 42056, 42058 and the surgical hub 42052 may not be the same performance level. In examples, some of the connections between the surgical system modules 42054, 42056, 42058 may provide redundant pathways of communication that may be used cooperatively. In examples, there may be daisy chain coupling of surgical system modules 42054, 42056, 42058. There may be a coupling hierarchy based on critical functionality of certain surgical system modules.

In examples, the surgical system 42050 may provide one-way monitoring communication for use in controlling aspects of another smart system. In an example, one or more of the surgical system modules 42054, 42056, 42058 may be non-smart surgical system modules, semi-smart surgical system modules, smart surgical system modules, and/or intelligent surgical system modules.

In an example, the surgical system 42050 may include a dumb (or non-smart) surgical system module that may be connected to other surgical system modules. The dumb surgical system module may be power independent and connected to its own power source. For example, surgical system module 42056 may have its own power source 42084 that is separate from the other power sources 42080 and 42082, or 42086 that powers other surgical system modules 42054 or 42058 respectively.

In an example, the surgical system 42050 may include a non-smart surgical system module that may be connected to other surgical system modules. The non-smart surgical system module may be power independent from the surgical system modules connected to the surgical hub 42052. The non-smart module may have one way data flow with minimal communications with the surgical system modules.

In an example, the surgical system 42050 may include of a semi-smart surgical system module that may be connected to other surgical system modules. The semi-smart surgical system module may include two way communication with the surgical system modules. The semi-smart surgical system module may monitor the input power. The semi-smart surgical system module may have minimal command and control of its functions.

In an example, the surgical system 42050 may include a smart surgical system module that is connected to the other surgical system modules. The smart surgical system module may include two way communication with the surgical system modules which may include a bipolar generator. The smart surgical system module may have enhanced command and control of its functions. The smart surgical system module may monitor its inputs and outputs.

In other examples, the surgical systems described herein may include an intelligent surgical system module. The intelligent surgical system module may include multiple communication paths. The intelligent surgical system module may have full command and control of its functions.

The surgical system 42050 may provide integrated monitoring enabling non-smart surgical system modules to be used with smart surgical system modules. The integrated monitoring may include monitoring for the interference of non-smart surgical system modules during the activation of smart surgical system modules. This may prevent accidental simultaneous energy activation of non-smart surgical system modules and smart surgical system modules. In examples, the integrated monitoring may prevent a portion of the non-smart surgical system modules and the smart surgical system modules from activating simultaneously. For example, the ultrasonic advanced energy portion of a smart surgical system module may be used in combination with a monopolar radio frequency application from another surgical system module while preventing the smart surgical system module's radio frequency portion to be used simultaneously with the monopolar radio frequency application. For example, the surgical system module 42054 may be a non-smart surgical system module and surgical system module 42056 may be a smart surgical system module. The surgical system modules 42054 and 42056 may work independently from one another or together during certain times of certain surgical procedures. The smart module may incrementally control the non-smart module. In examples, the surgical system modules 42054, 42056 may be a generator and smoke evacuator respectively. The generator may generate a step electrical potential output to indicate the increase airflow, the activation of the energy device to increment the smoke evacuator, or the increase/decrease of speed without other cooperative communication.

In an example, one of the surgical system modules, for example, surgical system module 42054 may have an ability to be connected to more than one (e.g., two) power sources 42080 and 42082. The surgical system module 42054 may be receivable in a backplane with two outlets where the power sources 42080 and 42082 may be available for connection. The power sources 42080 and 42082 may be connected to the two outlets of the backplane. Each of the power sources 42080 and 42082 may be a part of an independent power circuit. The independent power circuits may be in communication or isolated from each other. Each of the power sources 42080 and 42082 may be an AC power source or a DC power source. In an example, the surgical hub 42052 or the surgical system module 42054 may determine that the surgical system module 42054 to be powered on may require power from both the available power sources 42080 and 42082. In such an example, based on at least that the surgical system module 42054 may require power from both the available power sources 42080 and 42082, the surgical system module 42054 may be powered using both the power sources 42080 and 42082.

The surgical system 42050 (as illustrated in FIG. 10) may include a configuration to a surgical hub port available when the surgical modules 42054, 42056, 42058 in communication with the surgical hub 42052 by sharing a bus. Each surgical module 42054, 42056, 42058 may have a specific identification. The surgical modules 42054, 42056, 42058 may be in close proximity to each other to align well with a serial protocol. In examples, the surgical system 42050 may be set up in a primary source/secondary source configuration. The surgical hub 42052 may be the primary source and the surgical modules 42054, 42056, 42058 may be the secondary sources. The surgical hub 42052 may be connected to the surgical modules 42054, 42056, 42058 via a first port 42060. The surgical modules 42054, 42056, 42058 may directly connect to each other via a second port 42062. Extra cables 42064, 42066, 42068 may allow data pass from the surgical modules 42054, 42056, 42058. Although the extra cables 42064, 42066, 42068 are shown in the figure to be connected via the backplane 42078, in some cases, the extra cables 42064, 42066, 42068 may be connected between the surgical modules 42054, 42056, 42058 on the front side of the surgical modules 42054, 42056, 42058.

In an example, the extra cables 42064, 42066, 42068 may be enabled to establish an analog connection between the surgical system modules 42054, 42056, 42058, for example, by sensing analog aspects of the connection. In an example, the extra cables 42064, 42066, 42068 may be configured to establish a digital connection between the surgical system modules 42054, 42056, 42058.

In an example, the communication interface between the surgical system modules 42054, 42056, 42058 may be configured to establish a serial connection via a serial bus using a serial protocol. In an example, the communication interface between the surgical system modules 42054, 42056, 42058 may be configured to establish a communication path using for example a serial peripheral interface (SPI). In an example, multiple communication paths may be established, for example, one communication pathway (e.g., the primary communication pathway) may be a SPI communication bus between the surgical hub 42052 and the surgical system modules 42054, 42056, 42058. A secondary communication pathway may be established using a surgical module to surgical module serial bus.

In an example, data may pass to the surgical hub 42052 via the second port 42062. In examples, the data may not pass to the surgical hub 42052 via the second port 42062. Certain functions and data transfers may be isolated from the surgical hub 42052 via the second port 42062. Certain functions and data transfers may be communicated to the surgical hub 40602 via the first port 42060. In examples, the second port 42062 between each of the surgical modules 42054, 42056, 42058 may be an additional slow communication portal. In examples, the second port 42062 may include an auxiliary data path from a surgical module 42054, 42056, 42058 to the surgical hub 42052.

In an example, each of the surgical system modules 42054, 42056, 42058 and the backplane 42078 may be connected to a common ground 42088. In an example, the surgical hub may detect that the one of the surgical system modules 42054 may not be connected to the common ground 42088 and/or the connection to common ground is interrupted. The surgical system module 42054 may send a notification message via the control plane 42070 to the surgical hub 42052. The surgical hub may then present (e.g., display) the control plane message to a user or an HCP.

In an example (e.g., when a new surgical procedure is initiated), after detecting that the surgical system module 42054 is not connected to the common ground 42088, the surgical system module 42054 may be disabled. The surgical system module 42054 may be disabled based on a control program received by the surgical system module 42054 from the surgical hub 42052.

In an example (e.g., when a surgical procedure is being performed), after detecting that the surgical system module 42054 is not connected to the common ground 42088, the surgical system module 42054 may not be disabled. The surgical system module 42054 may be disabled once the surgical procedure being performed ends or based on situational awareness and/or surgical plan, the surgical hub 42052 determines that the module will no longer be needed during the ongoing surgical procedure.

Systems and methods may be provided for handling loss of communication between the surgical hub and the system modules/modular devices or between the system modules/modular devices. In an example, either the surgical hub or one or more of the system modules and/or the modular devices associated with a surgical system may detect a loss of communication. The loss of communication may be detected based on interrupted and/or irregular communications on one or more communication modules associated with a system module or modular device. A loss of communication, for example, detected by a system module or a modular device may be indicated using a visual, audio, or an audiovisual indication. The indication of an alarm may be based on the severity of the communication loss. For example, a total loss of communication on a critical surgical system module may be indicated by all means possible including, for example, providing the information to one or more HCPs via the main display or other displays present in an OR.

Figure 11:
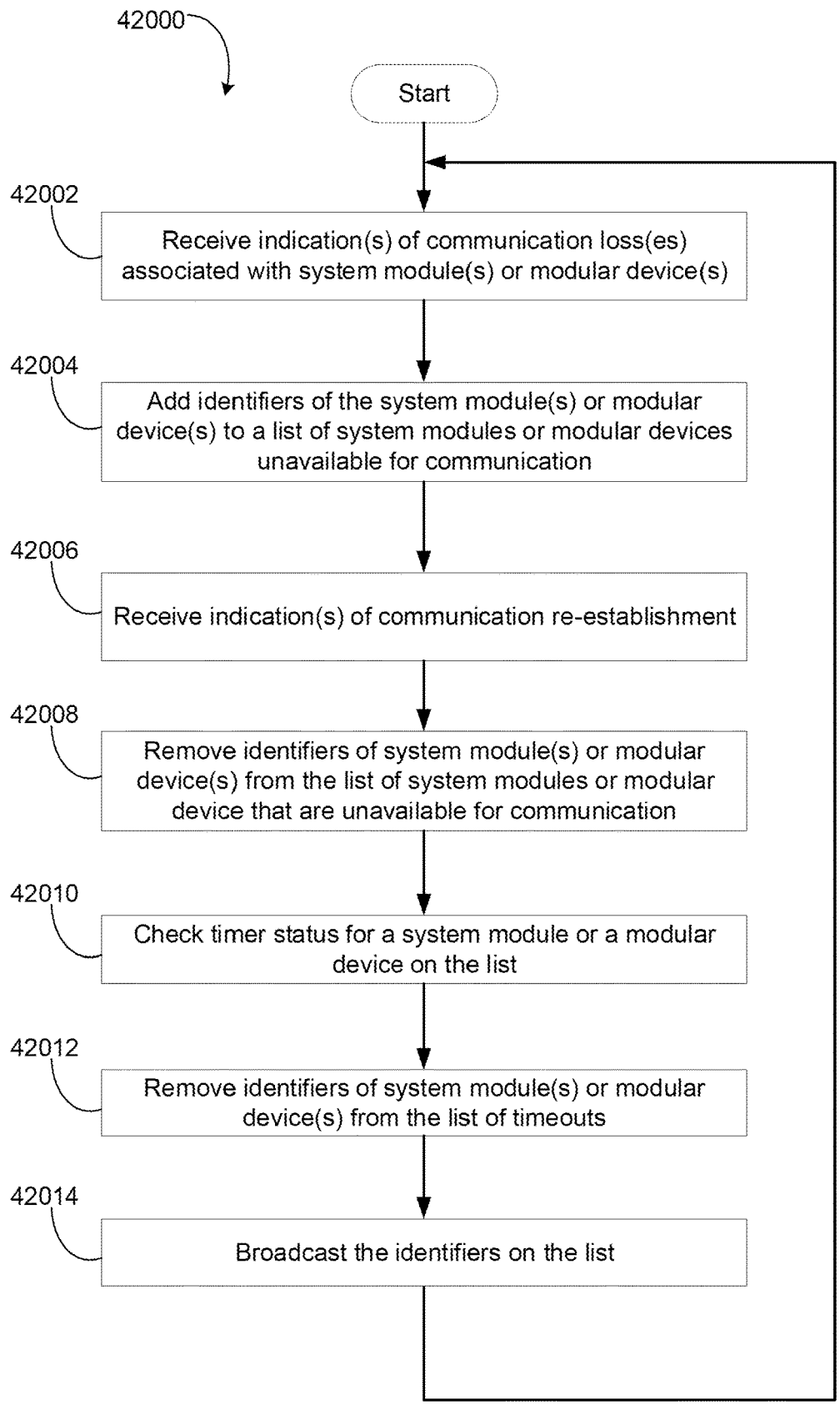
FIG. 11 is a flow diagram illustrating an exemplary process of a loss of communication between system modules and/or modular devices.

FIG. 11 illustrates processing of a loss of communication between system modules and/or modular devices, 42000. At 42002, a surgical hub may receive, from one or more system modules or modular devices, one or more indication(s) of communication loss(es) associated with a system module or a modular device. At 42004, the surgical hub may add identifiers associated with the system modules or modular devices to a list of system modules or modular devices that are unavailable for communication. The surgical hub may send (e.g., as a broadcast or a unicast message) the updated list of system modules or modular devices that are unavailable for communication to other system modules or modular devices and/or a display unit for displaying the loss of communication of a system module or a modular device.

At 42006, the surgical hub may receive, from one or more system modules or modular devices, one or more indication(s) of communication re-establishment of a communication loss associated with a system module or a modular device. At 42008, the surgical hub may remove identifiers associated with the system modules or modular devices from the list of system modules or modular devices that are unavailable for communication. The surgical hub may then send (e.g., as a broadcast or a unicast message) the updated list of system modules or modular devices that are unavailable for communication to other system modules or modular devices and/or a display unit for displaying the loss of communication of a system module or a modular device. In an example, the surgical hub, based on situational awareness and/or locational awareness, may determine that the system module or the modular device with loss of communication is to be used in a critical step of a surgical procedure. The surgical hub may escalate the severity associated with a loss of communication state of the system module or the modular device. The surgical hub may send the escalated loss of communication status message associated with the system module or the modular device to the main display for immediate attention.

The surgical hub (e.g., using an identifier) may start a timer associated with a system module or a modular device. For example, the surgical hub may start a timer a communication loss or communication re-establishment associated with a system module or a modular device. At 42010, the surgical hub may check the timer status associated with the system module or the modular device. At 42012, the surgical hub may remove an identifier associated with the system module or the modular device, for example, if the timer associated with the system module or the modular device crosses a threshold (e.g., a predefined threshold). At 42014, the surgical hub may send (e.g., broadcast) the identifiers on the list on of system modules or modular device that are unavailable for communication to other surgical hubs, system modules, modular device, and/or display devices.

In an example of a system module or a modular device with redundant communication connections that reports a communication loss regarding one of its redundant communication connections, the surgical hub may send a control program to the system module or the modular device to activate and/or use the second available communication connection. In an example, a system module or a modular device may autonomously activate the second available communication connection, for example, after detecting a loss of communication one of the communication connections.

In an example, after detecting a loss of communication on one of the communication interfaces, a system module or a modular device may continue to operate in the last connected state.

Surgical procedures may be performed by different HCPs at different locations. For a given surgical procedure, one or more system modules, modular devices and/or one or more parameters associated with the system modules or modular devices that are part of a surgical system may be selected, for example, as an attempt to realize a desired outcome. In an example, for a given surgical procedure which utilizes energy supplied by a generator, an HCP may rely on experience for determining a modular device or a mode of a modular device to utilize, the output power level to utilize, the application duration of the energy, etc., in order to attempt to realize the desired outcome. To increase the likelihood of realizing desired outcomes for a plurality of different surgical procedures, each HCP may be provided with best practice recommendations, system module and/or modular device selection, and/or settings for the system modules and/or the modular devices. Such a selection of best practice recommendations, system modules and/or modular device selection, and/or settings for the system modules and/or modular devices may be based on relationships (e.g., important relationships) identified within large, accurate data sets of information associated with multiple surgical procedures performed in multiple locations over time.

In an example, a surgical hub may identify an optimized or a preferable combination of system modules and/or modular devices and/or configuration associated with the system modules and/or modular devices for a surgical procedure. The system modules and/or modular devices may be plugged into the surgical system. The system modules and/or modular devices may be wirelessly connected to the surgical hub or may be present within the surgical hub's surroundings (e.g., within an OR) ready to be connected to the surgical hub. The surgical hub may identify the optimized or the preferable combination of system modules and/or modular devices and their configuration based on one or more of the following: the interfacing system modules and/or modular devices, the awareness of the surgical procedure plan, the surgical procedure type (e.g., thoracic vs colorectal), and a surgeon's previous preferences. In an example, the surgical hub may identify the optimized or the preferable combination of system modules and/or modular devices and their configuration based on a risk/harm database.

Figure 12:
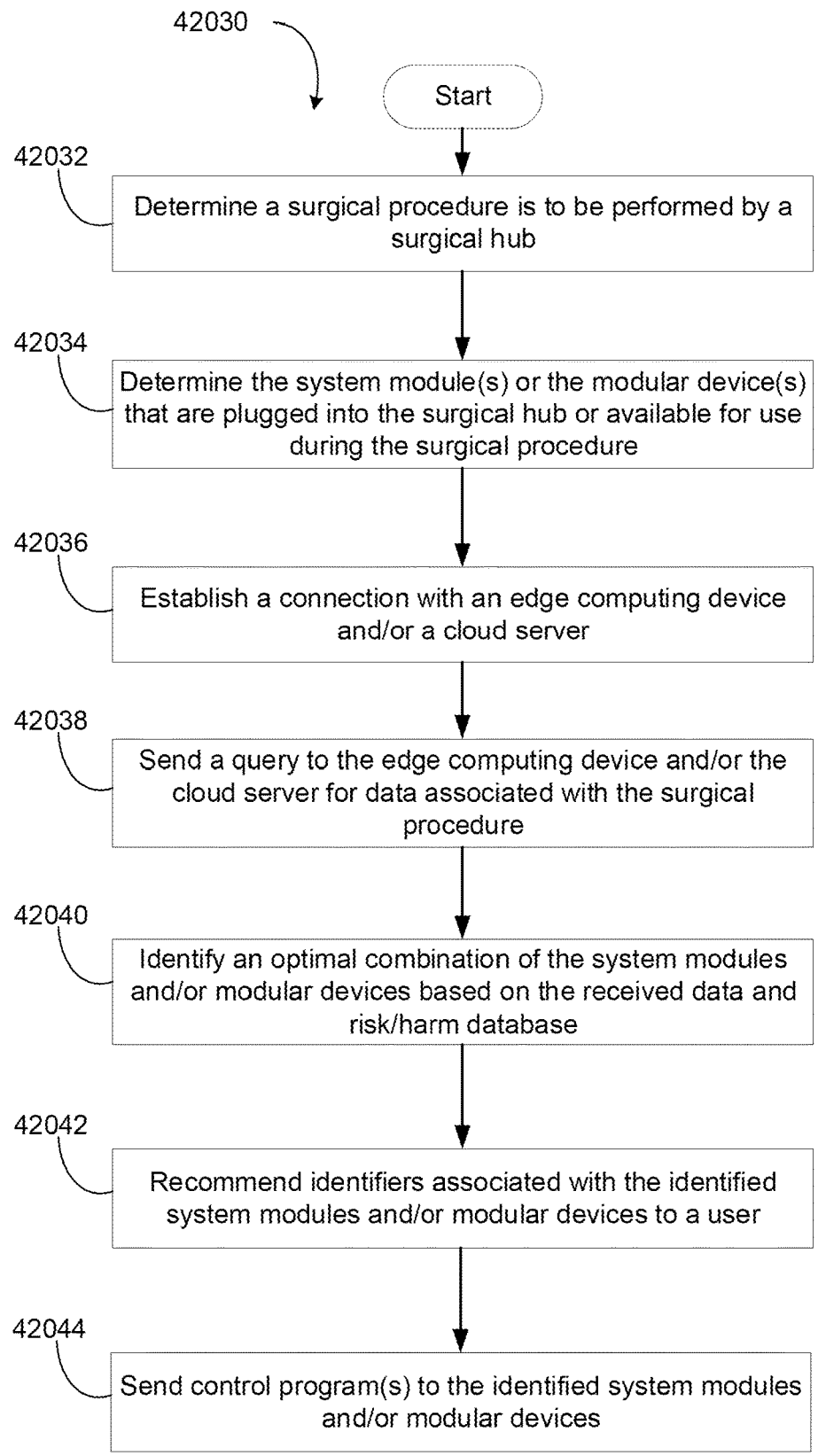
FIG. 12 is a flow diagram illustrating an example of a surgical hub identifying an optimal combination of system modules and/or modular devices.

FIG. 12 illustrates an example of a surgical hub identifying an optimal combination of system modules and/or modular devices. At 42032, a surgical hub may determine that a surgical procedure is to be performed by the surgical hub in an OR.

At 42034, the surgical hub may determine the system modules and/or modular devices that may be plugged into a surgical system including the surgical hub or available for use during the surgical procedure. At 42036, the surgical hub may establish a connection with an edge computing device and/or a cloud server.

At 42038, the surgical hub may send a query to the edge computing device or the cloud server requesting for surgical procedure data associated with the surgical procedure. At 42040, the surgical hub may identify an optimal combination of the system modules and/or the modular devices to be used for performing the surgical procedure. The surgical hub may identify the optimal combination of the system modules and/or the modular devices to be used for performing the surgical procedure at least based on the surgical procedure to be performed, the location of the surgical hub and/or where the surgical procedure is being performed, and/or the surgical procedure data received from the server. The optimal combination identified may further be based on a database identifying the risks/harms associated with the combination. For example, a surgical hub may identify three energy devices plugged or available for use during a surgical procedure—an ultrasonic energy generator, a bipolar RF energy generator, and a monopolar RF energy generator.

At 42042, the surgical hub may provide a recommendation including identifiers associated with the optical combination of the system modules and/or modular devices to the user (e.g., an HCP).

The surgical hub may determine whether it is configured with the identified optimal combination of the system modules and/or the modular devices. At 42044, the surgical hub may send control programs to the identified system modules and/or modular devices, for example, if the surgical hub determines that it is not configured with the identified optimal combination of the system modules and/or the modular devices.

What is claimed is:

1. A surgical system comprising a processor that is configured to perform at least:
   determine a first control scheme that is configured to control a set of modules associated with a surgical hub;
   receive an input from one of the set of modules or a device located that is located within bounds of an operating room;
   determine at least one of a safety status level or an overload status level of the surgical hub is higher than its threshold value;
   determine, based on the input received from one of the modules or from the device and the determination that at least one of the safety status level or the overload status level of the surgical hub is higher than respective thresholds, a second control scheme to be configured to control the set of modules associated with the surgical hub; and
   send a control program to one or more modules of the set of modules to establish the second control scheme.

2. The surgical system of claim 1, wherein the first control scheme or the second control scheme is one of a cooperative control scheme, a notification control scheme, an antagonistic control scheme, or a hierarchical control scheme.

3. The surgical system of claim 2, wherein the processor being configured to establish the cooperative control scheme comprises the processor being configured to enable a first module of the set of modules to communicate with a second module of the set of modules such that a condition in the first module impacts operation of the second module.

4. The surgical system of claim 2, wherein the processor being configured to establish the notification control scheme comprises the processor being configured to enable a first module of the set of modules to notify a second module of the set of modules about an occurrence of an event or a parameter associated with one of the functions of the first module.

5. The surgical system of claim 2, wherein the processor being configured to establish the antagonistic control scheme comprises the processor being configured to prioritize a first task associated with a first module of the set of modules over a second task associated with a second module of the set of modules.

6. The surgical system of claim 5, wherein the processor being configured to prioritize the first task comprises the processor being configured to prioritize the first task based on at least one of importance of a module, function of the first task, or a predefined configured value.

7. The surgical system of claim 2, wherein the processor being configured to establish the hierarchical control scheme comprises the processor being configured to establish a hierarchy of control between a first module of the set of modules and a second module of the set of modules.

8. The surgical system of claim 1, wherein the second control scheme is determined based on one or more of needs of the surgical hub, priorities of the modules, and capacity of the modules or capacity of the surgical hub.

9. The surgical system of claim 1, wherein the processor is configured to:
   determine communication interfaces associated with the modules; and
   control the communication interfaces, wherein the communication interfaces are controlled based on capabilities, interferences, and data being communicated.

10. The surgical system of claim 1, wherein the processor is configured to identify configuration of one of a module, an equipment, or a device using one of an electronic communication or a visualization from in an operating room (OR) camera.

11. The surgical system of claim 10, wherein the processor is configured to adapt one of a communication limit, an interconnectivity, a master-slave control operation, a timing, or a data passing pathway based on the identified configuration of the one of the module, the equipment, or the device.

12. The surgical system of claim 10, wherein the processor being configured to identify configuration of one of the module, the equipment, or the device comprises the processor being configured to identify configuration of one of the module, the equipment, or the device based on risk/harm database.

13. A method comprising:
   determining a first control scheme that is configured to control a set of modules associated with a surgical hub;
   receiving an input from one of the set of modules or a device located that is located within bounds of an operating room;
   determining at least one of a safety status level or an overload status level of the surgical hub is higher than its threshold value;
   determining, based on the input received from one of the modules or from the device and the determination that one of the safety status level or the overload status level of the surgical hub is higher than respective thresholds, a second control scheme to be configured to control the set of modules associated with the surgical hub; and
   sending a control program to one or more modules of the set of modules to establish the second control scheme.

14. The method of claim 13, wherein the first control scheme or the second control scheme is one of a cooperative control scheme, a notification control scheme, an antagonistic control scheme, or a hierarchical control scheme.

15. The method of claim 14, wherein establishing the cooperative control scheme comprises enabling a first module of the set of modules to communicate with a second module of the set of modules such that a condition in the first module impacts operation of the second module.

16. The method of claim 14, wherein establishing the notification control scheme comprises enabling a first module of the set of modules to notify a second module of the set of modules about an occurrence of an event or a parameter associated with one of the functions of the first module.

17. The method of claim 14, wherein establishing the antagonistic control scheme comprises prioritizing a first task associated with a first module of the set of modules over a second task associated with a second module of the set of modules.

18. The method of claim 17, wherein the first task is prioritized prioritization is based on at least one of importance of a module, function of the first task, or a predefined configured value.

19. The method of claim 14, wherein establishing the hierarchical control scheme comprises the establishing a hierarchy of control between a first module of the set of modules and a second module of the set of modules.

20. The method of claim 13, wherein the second control scheme is determined based on one or more of needs of the surgical hub, priorities of the modules, and capacity of the modules or capacity of the surgical hub.

* * * * *